US006444791B1

(12) United States Patent
Quay

(10) Patent No.: US 6,444,791 B1
(45) Date of Patent: Sep. 3, 2002

(54) METHODS AND COMPOSITIONS FOR THE TREATMENT OF KERATOCONUS USING PROTEASE INHIBITORS

(75) Inventor: Steven C. Quay, Edmonds, WA (US)

(73) Assignee: K-Quay Enterprises, LLC, Edmonds, WA (US)

( * ) Notice: Subject to any disclaimer, the term of this patent is extended or adjusted under 35 U.S.C. 154(b) by 0 days.

(21) Appl. No.: 09/695,774

(22) Filed: Oct. 24, 2000

Related U.S. Application Data

(60) Provisional application No. 60/161,879, filed on Oct. 27, 1999.

(51) Int. Cl.[7] .......................... A61K 35/14; A61K 38/16; A61K 9/127; C07K 14/00; C07K 17/00
(52) U.S. Cl. ........................ 530/380; 530/381; 530/412; 530/350; 514/12; 514/912; 424/78.04; 424/94.64; 424/94.65; 424/94.66; 424/94.67; 424/450; 424/489
(58) Field of Search ........................ 424/78.04, 94.64, 424/94.65, 94.66, 94.67, 450, 489; 514/912, 12; 530/350, 380, 381, 412

(56) References Cited

U.S. PATENT DOCUMENTS

| 5,290,762 A |   | 3/1994  | Lezdey et al. .................. 514/8      |
| 5,773,438 A | * | 6/1998  | Levy et al. ............... 514/237.8       |
| 5,876,709 A | * | 3/1999  | Itoh et al. ................. 424/78.04     |
| 5,892,112 A |   | 4/1999  | Levy et al. .................. 564/133      |
| 5,929,097 A |   | 7/1999  | Levin et al. ................. 514/351      |
| 5,962,481 A |   | 10/1999 | Levin et al. ................. 514/352      |

FOREIGN PATENT DOCUMENTS

| JP | 09003094 | * | 1/1997 |

OTHER PUBLICATIONS

Berman et al., *Invest. Opthalmol. Vis. Sci.* 12:759–770, 1973.
Bouaboula et al., *J. Biol. Chem.* 267:21830–21838, 1992.
Brown et al., *Curr. Eye Res.* 12:571–578, 1993.
Edrington, et al., "Keratoconus," in *Corneal Disease Update*, Classe, JG, ed., Optometry Clinics, vol. 4, No. 3, Apple & Lange, Norwalk, CT, 1995.
Fabre et al., *Curr. Eye Res.* 7:585–592, 1991.
Findlay et al., *Endocrinology* 108:2129–2135, 1981.
Girard et al., *Invest. Ophthalmol. Vis. Sci.* 32:2441–2454, 1991.
Kao et al., *Biochem. Biophys. Res. Commun.* 107:929–936, 1982.
Kenney et al., "Altered gelatinolytic activity by keratoconus corneal cells," *Biochem. and Biophys. Res. Comm.* 161(1):353–357, 1989.
Prause, J. U., "Serum albumin, serum antiproteases and polymorphonuclear leucocyte neutral collagenolytic protease in the tear fluid of normal healthy persons," *Acta Ophthalmologica* 61:261–271, 1983.
Prause, J. U., "Serum albumin, serum antiproteases and polymorphonuclear leucocyte neutral collagenolytic protease in the tear fluid of normal healthy persons," *Acta Ophthalmologica* 61:272–282, 1983.
Rahi et al., *J. Opthalmol.* 61:761–764, 1977.
Rehany et al., "Collagenolytic activity in Keratoconus," *Annals of Ophthalmology* 751–754, 1982.
Sack, et al., "Diurnal Tear Cycle: Evidnce for a nocturnal inflammatory consitutive tear fluid," *Investigative Ophthalmology & Visual Science* 33(3):626–640,1992.
Sathe et al., "Identification, origins and the diurnal role of the principal serine protease inhibitors in human tear fluid," *Current Eye Research* 17:348–362, 1998.
Sawaguchi et al., "Three–Dimensional Scanning Electron Microscopic Study of Keratoconus Corneas," *Arch. Ophthalmol.* 116:62–68, 1998.
Sawaguchi et al., "α–1 proteinase inhibitor levels in keratoconus," *Exp. Eye Res.* 50:549–554, 1990.
Sawaguchi et al., "α–2–Macroglobulin levels in normal human and keratoconus cornease," *Invest. Ophthal. & Vis. Sci.* 35(12):4008–4014, 1994.
Sawaguchi, et al., "Lysosomal Enzyme Abnormalities in Keratoconus," *Arch. Ophthalmol.* 107:1507–1510, 1989.
Smith et al., "Over–expression of a gelatinase A activity in keratoconus," *Eye* 9:429–433, 1995.
Tuori, et al., "The immunohistochemical composition of corneal basement membrane in keratoconus," *Current Eye Ressearch* ??.
Whitelock et al., "Expression of Transcription Factors in Keratoconus, a Cornea–Thinning Disease," *Biochemical and Biophysical research Communications* 235:253–258, 1997.

(List continued on next page.)

*Primary Examiner*—Karen Cochrane Carlson
*Assistant Examiner*—Chih-Min Kam
(74) *Attorney, Agent, or Firm*—Woodcock Washburn LLP

(57) ABSTRACT

Compositions and methods for treating corneal diseases mediated by elevated protease activity include ocular administration of protease inhibitors. One or more protease inhibitors selected from an aspartic, serine, cysteine, or metalloprotease inhibitor are administered to an ocular fluid, surface, or tissue, preferably by topical administration, to inhibit proteolytic activity associated with a corneal disease or condition, for example keratoconus. Antiproteolytic formulations of the invention may include carriers that prolong the retention and/or enhance delivery of the protease inhibitor. These formulations can also include other therapeutic agents such as antiinflammatory or antibiotic drugs. In preferred aspects of the invention, antiproteolytic formulations are administered during periods of closed eye tear production. Also provided within the invention are implant devices for corneal delivery of a protease inhibitor.

6 Claims, No Drawings

OTHER PUBLICATIONS

Whitelock, et al., "Cathepsin G., Acid Phosphatase, and α1–Proteinase Inhibitor Messenger RNA evels in Keratoconus Corneas," *Investigative Ophthalmology & Visual Science* 38(2):529–534, 1997.

Wilson et al., *Exp. Eye Res.* 62:325–337, 1996.

Wollensak and Buddecke, "Biochemical Studies on Human corneal Proteoglycans—A Comparison of Normal and Keratoconic Eyes," *Graefe's Arch. Clin. Exp. Ophthalmol.* 228:517–523, 1990.

Yue et al., "Heterogeneity in Keratoconus: Possible Biochemical Basis" *Proc. Soc. Exp. Biol. Med.* 175:336–341, 1984.

Zhou et al., "Expression of degradative enzymes and protease inhibitors in corneas with keratoconus," *Invest. Ophthal. & Vis. Sci.* 39(7):1117–1124, 1998.

Zhou et al., *Invest. Ophthalmol. Vis. Sci.* 37(Suppl):S1017, 1996.

* cited by examiner

METHODS AND COMPOSITIONS FOR THE TREATMENT OF KERATOCONUS USING PROTEASE INHIBITORS

RELATED APPLICATION

This application claims the benefit of U.S. Provisional Patent Application No. 60/161,879, filed by Dr. Steven C. Quay on Oct. 27, 1999.

BACKGROUND OF THE INVENTION

Keratoconus is a bilateral ocular disorder that progressively thins and distorts the central portion of the cornea toward a conic shape, typically leading to substantial visual impairment and corneal scarring. Distortion of the cornea in keratoconus results from decreased resilience and low mechanical strength of the corneal tissues (Wollensak et al., *Fortschr. Ophthalmol.* 84:28–32, 1987, incorporated herein by reference). These structural defects represent important pathogenetic factors in the disease (Edmund, *Acta Ophthalmol.* 66:134–140, 1988, incorporated herein by reference), however the mechanisms that cause these structural changes remain undefined.

To date, no specific tools have been developed to treat or prevent keratoconus. In the mildest cases, management involves the use of spectacles or soft contact lenses. More commonly, early stage management of keratoconus requires specially designed contact lenses that compensate visual defects and provide some structural support to correct corneal distortion. More advanced presentations are managed with rigid gas-permeable (RGP) contact lenses to minimize corneal distortion and correct irregular astigmatism (Koliopoulos et al., *Ann. Ophthalmol.* 13(7):835–7, 1981, incorporated herein by reference). If satisfactory wearing time is not achieved with contact lens, or if the contact lens-corrected vision is not adequate (which may result from corneal scarring or poor fitting of the steeply sloped cone) keratoplasty is indicated.

Even with the aid of the foregoing management tools, the vision of patients with keratoconus often deteriorates beyond correction. At this point the replacement of corneal tissue by transplantation becomes the indicated treatment option. Corneal transplantation is necessary for 10% to 20% of patients with keratoconus (Kennedy et al., *Am. J. Ophthalmol.* 101(3):267–73, 1986; and Smiddy et al., *Ophthalmology* 95:487–92, 1988, each incorporated herein by reference). However, corneal transplantation is attended by high costs, limitation of the supply of suitable corneas, and substantial risks, including risks of adverse sequelae from anesthesia, transplant failure, and transmission of tissue-borne pathogens (e.g., HIV virus) from donor tissue to the transplant recipient.

In addition to visual defects, the medical history of keratoconus patients often elicits allergic or systemic conditions. Atopic disease (allergy) is present in approximately 35% of cases (Rahi et al., *Br. J. Ophthalmol.* 61:761–4, 1977, incorporated herein by reference). Eye rubbing, possibly a response to allergic discomfort, is reported by 20% of patients with keratoconus (Ridley, *Br. J. Ophthalmol.* 45:631, 1961, incorporated herein by reference). In addition, keratoconus has been associated with inherited systemic diseases such as Down syndrome, Lebers congenital amaurosis, osteogenesis imperfecta, and connective tissue disorders such as Ehier-Danlos syndrome.

Despite extensive clinical and research efforts, no definitive etiology has emerged for patients presenting with a diagnosis of keratoconus. Some evidence suggests that a genetic component is involved (Rabinowitz et al., *Arch. Ophthalmol.* 108:365–371, 1990; and Jacobs et al., *Int. Ophthalmol. Clin.* 33:249–260, 1993, each incorporated herein by reference). Other reports suggest that environmental conditions, such as excessive eye rubbing or contact lens wearing, contribute to the disease (Coyle, *Am. J. Ophthalmol.* 97:527–528, 1984; and Macsai et al., *Arch. Ophthalmol.* 108:534–538, 1990, each incorporated herein by reference). Yet additional causes have been proposed, including atopic disease and systemic conditions.

The prevalence of atopic disease, such as hay fever and asthma, is approximately three times more common for patients with keratoconus when compared with a matched control group (Rahi et al., *Br. J. Ophthalmol.* 61:761–4, 1977, incorporated herein by reference). Eye rubbing, perhaps a response related to the allergy, is also more frequently exhibited by patients with keratoconus (Ridley, *Br. J. Ophthalmol.* 45:631, 1961, incorporated herein by reference). However, a causal association between allergy and/or eye rubbing, and the onset or progression of keratoconus, has not been established.

Other reports in the literature suggest that rigid contact lens wear is a causal factor in some cases of keratoconus (Macsai et al., *Arch. Ophthalmol.* 108:534–8, 1990, incorporated herein by reference). This finding is difficult to substantiate, because keratoconus patients may self-select contact lens wear due to their refractive error or patient dissatisfaction with spectacles.

A variety of systemic conditions have also been associated with keratoconus. Exemplary conditions include connective tissue disease, such as Ehlers-Danlos Rieger's, Crouzon's, and Marfan's syndromes. In addition, keratoconus has been diagnosed in up to 6% of patients with Down syndrome (Skeller et al., *Acta. Ophthalmol.* 29:149–61, 1951, incorporated herein by reference).

With regard to possible genetic factors, keratoconus has been shown to carry a hereditary component in approximately 6% to 8% of patients (Kennedy et al., *Am. J. Ophthalmol.* 101(3):267–73, 1986, incorporated herein by reference). In this context, Rabinowitz et al. (*Arch. Ophthalmol.* 108:365–71, 1990, incorporated herein by reference), have used videokeratographs to construct family pedigrees to determine modes of keratoconus heredity. The genetic component of keratoconus can be either dominant or recessive. However, the genotype of autosomal dominant is most common.

Despite the puzzling etiology of keratoconus, researchers continue to seek answers regarding the basic mechanisms underlying the onset and progression of this disease. However, to date most studies have focused on the morphological, i.e., histological and ultrastructural, changes associated with keratoconus. In this regard, it has long been noted that keratoconic corneas exhibit various ultrastructural defects, including fragmentation of Bowman's layer, fragmentation of the epithelial cell basement membrane, and fibrillation of the anterior stroma (Teng, *Am. J. Ophthalmol.* 55:1847, 1963; Chi et al., *Am. J. Ophthalmol.* 42:847–60, 1956; and Bron et al., *Trans. Ophthalmol. Soc. UK* 98:393–6, 1978, each incorporated herein by reference). Possible causes of these defects have been suggested to include changes in the metabolism and composition of extracellular matrix materials (ECMs).

Bowman's layer is an acellular matrix at the interface between the corneal epithelium and the stroma. It links the epithelial basement membrane and the stroma proper and may be crucial for epithelial attachment and function. During human corneal epithelial development, a distinct Bowman's layer is formed at 19 weeks (Tisdale et al., *Invest. Ophthalmol. Vis. Sci.* 29:727–736, 1988, incorporated herein by reference). After birth, the thickness of Bowman's layer remains unchanged. Components of Bowman's layer are believed to be synthesized by both corneal epithelial and stromal cells, and an epithelial-stromal interaction is suggested to be a major factor in the formation of Bowman's layer (Hay, *Int. Rev. Cytol.* 63:263–322, 1980, incorporated herein by reference).

Several years after radial keratotomy in human corneas, a Bowman's layer-like structure is formed underneath epithelial plugs that extend into the stroma (Melles et al., *Arch. Ophthalmol.* 113:1124–1130, 1995, incorporated herein by reference). The collagen fibrils in Bowman's layer are of relatively small diameter and are randomly arranged. In the underlying corneal stroma, the resident stromal cells are responsible for the maintenance and organization of the collagens. However, considering that Bowman's layer is acellular, the organization and maintenance of collagens at this site remains unexplained. One possibility is that these functions are performed by the sparse stromal cells that transverse into Bowman's layer. Cytokines have also been suggested to play a role in collagen maintenance in Bowman's layer. In keratoconus, the collagen maintenance function of stromal cells and/or cytokines may be disturbed for both Bowman's layer and for the stroma.

For more than a decade, evidence has been accumulating to suggest that biochemical and/or molecular changes in the metabolism and/or makeup of extracellular matrix materials (ECMs), such as collagen, may lead to the above noted corneal structural changes associated with keratoconus. To evaluate this aspect of the disease, one comparative study analyzed collagen types I, III, IV and V in normal versus keratoconic corneas (see, e.g., Oxlund et al., *Acta. Ophthalmol.* 63:666–669, 1985, incorporated herein by reference). This study found no differences in amino acid composition, nor in the type and number of collagen cross-links, between these groups. Other studies reported changes in the spatial distribution and specific immunostaining of the various collagen types between normal and keratoconic corneas (Ihme et al., *Exp. Eye Res.* 36:625,631, 1983; Nakayasu et al., *Ophthalmic Res.* 18:1–10, 1986; Yue et al., *Proc. Soc. Exp. Biol. Med.* 175:336–341, 1984; and Zimmermann et al., *Exp. Eye Res.* 46:431–442, 1988, each incorporated herein by reference). However, one study reported increased content of type V collagen in keratoconic corneas (Yue et al., *Biochim. Biophys. Acta.* 755:318–325, 1983, incorporated herein by reference).

Other studies directed to protein metabolism and content in keratoconic corneas produced different results compared with the above cited studies. For example, some reports conclude that keratoconic tissues exhibit higher levels of protein and increased incorporation of protein precursors (e.g., [$^3$H]-proline) into all cell layers compared with normal corneal tissues (Rehany et al., *Invest. Ophthalmol. Vis. Sci.* 25:1254–1257, 1984; Critchfield et al., *Exp. Eye Res.* 46:953–963, 1988; and Wollensak et al., *Graefe's Arch. Clin. Exp. Ophthalmol.* 228:517–523, 1990, each incorporated herein by reference). In contrast, Sawaguchi et al. conclude that collagen content in some cases of keratoconus is reduced compared with that of normal human corneas (*Arch. Ophthalmol.* 116:62–68, 1998, incorporated herein by reference). These authors also report abnormal, loosely packed and randomly oriented collagen fibrils in the corneal stroma of some keratoconus patients, which is proposed to reflect reduced collagen density. Further complicating this model, Yue et al. report that corneal specimens and cultured cells from affected persons show a reduction in overall protein levels compared with normal controls (*Proc. Soc. Exp. Biol. Med.* 175:336–341, 1984, incorporated herein by reference). However, collagen content is normal in some specimens, while the levels of collagenous proteins is substantially reduced in others, suggesting that pathology of the disease's is in fact "heterogeneous".

Reports of reduced protein levels in keratoconic corneas have generated numerous hypotheses that the disease may be causally linked to changes in the degradative metabolism of extracellular macromolecules (Yue et al., *Proc. Soc. Exp. Biol. Med.* 175:336–341, 1985, incorporated herein by reference). In this context, researchers have proposed a variety of possible mechanisms, including changes in the structure, expression, and/or activity of degradative enzymes, and alterations in the levels and/or activity of enzyme inhibitors. Because interacting systems of degradative enzymes and their inhibitors are normally under tight regulatory controls, alterations in enzyme inhibitor balances may have a significant impact on the integrity of the cornea.

Studies aimed at defining degradative changes associated with keratoconus have yielded diverse, and often conflicting, results. A number of studies report increased levels of degradative enzymes associated with keratoconus (Sawaguchi et al., *Arch. Ophthalmol.* 107:1507–1510, 1989, incorporated herein by reference). For example, keratoconic corneas reportedly exhibit increased levels or activities of acid esterase, acid phosphatase, acid lipase, and cathepsins B and G (Sawaguchi et al., *Invest. Ophthalmol. Vis. Sci.* 35:4008–4014, 1994; Sawaguchi et al., *Arch. Ophthalmol.* 107:1507–1510, 1989; and Zhou et al., *Invest. Ophthalmol. Vis. Sci.* 39:1117–1124, 1998, each incorporated herein by reference). Also reported are higher collagenase and gelatinase activities in keratoconic tissues compared to normal corneal tissues (Kao et al., *Biochem. Biophys. Res. Commun.* 107:929–936, 1982, incorporated herein by reference). In light of these reports, some investigators propose that imbalances in protease/protease inhibitor levels may contribute to decreased protein levels and increased proteolytic activities associated with keratoconus. Additional investigations have reported decreases in the levels of certain proteolytic enzyme inhibitors, for example, α1-protease inhibitor (alp1) (Whitelock et al., *Invest. Ophthalmol. Vis. Sci.* 38:529–534, 1997; Sawaguchi et al., *Exp. Eye Res.* 50:549–554, 1990, each incorporated herein by reference), and α2-macroglobulin (α2-M) (see, e.g., Sawaguchi et al., *Arch. Ophthalmol.* 107:1507–1510, 1989; Sawaguchi et al., *Exp. Eye. Res.* 50:549–554, 1990; and Sawaguchi et al., *Invest. Ophthalmol. Vis. Sci.* 35:4008–4014, 1994, each incorporated herein by reference) in association with keratoconus.

However, the model of a protease/protease inhibitor imbalance as a pathogenic mechanism in keratoconus remains speculative. In this regard it is noteworthy that Yue et al., supra, conclude that, for the subset of keratoconus cases where collagen levels are actually reduced, the reduction is apparently due to decreased collagen synthesis rather than to an increase in protease activity or a decrease in protease inhibition. Other reports suggest that pathogenic changes associated with keratoconus, including increased collagenolytic activity, may be attributed to structural changes in the collagen proteins themselves, as opposed to altered collagen expression or elevated protease function (e.g., attributable to higher protease levels or activities, or decreased protease inhibitor levels or activities).

A substantial amount of research pertaining to degradative mechanisms in keratoconus has focused on a large class of proteolytic enzymes, known as matrix metalloproteases (MMPs). MMPs comprise a large class of enzymes known for their capacity to degrade extracellular matrix elements. This class includes a growing host of collagenases (e.g., MMP-1, MMP-8, MMP-13, and MMP-18), gelatinases (e.g., gelatinase A or MMP-2, and gelatinase B or MMP-9), and stromelysin (MMP-3). MMPs are generally secreted as proenzymes and must be activated for conversion into mature enzymes. MMP species and activities present in keratoconic corneas have been extensively examined.

Data obtained by assaying acyl transferase activity show that MMPs account for at least 95% of the total protease secreted by cultured keratocytes. The summated specific activity of MMPs is reported to be consistently and significantly higher in the culture media of keratoconic keratocytes than in media of other keratocyte cultures. Smith et al., *Eye* 9:429–433, 1995, incorporated herein by reference. More specifically, researchers have reported significantly increased collagenase and gelatinase activities associated with keratoconus, in both organ culture (Kao et al., *Biochem. Biophys. Res. Commun.* 107:929–936, 1982; and Rehany et al., *Ann. Opthalmol.*: 14:751–754, 1982, each incorporated herein by reference) and cell culture (Ihlainen et al., *Eur. J. Clin. Invest.* 16:78–84, 1984; and Kenney et al., *Biochem. Biophys. Res. Commun.* 161:353–357, 1989, each incorporated herein by reference) studies. However, at least one investigation using corneal extracts reported no difference between keratoconic and healthy control samples in either the total amount or types of gelatinases (Zhou et al., *Invest. Opthalmol. Vis. Sci.* 39:1117–1124, 1998, incorporated herein by reference). A subsequent study by Brown et al. reported that gelatinase activity was elevated in keratoconus extracts after chemical modification of inhibitory elements (*Curr. Eye Res.* 12: 571–8, 1993, incorporated herein by reference).

Although increased collagenase activity in keratoconus is expected to be associated with reduced collagen content in keratoconic corneas, widely varying results have been reported in this context. While some studies appear to demonstrate decreased collagen levels associated with the disease, others indicate that collagen levels remain unchanged. In addition, the results of Yue et al., supra, suggest that the disease is actually heterogeneous, with some cases associated with reduced collagen content and others not. These results militate against a causal relationship between collagen degradation and keratoconus. Specifically, because Yue et al. found no significant differences in medical histories and severity of clinical symptoms between the different groups studied, the observed variation in collagen content in one group of keratoconus patients does not appear to be directly linked to disease progression.

In situ zymography studies have also been conducted to further assess the net functional activity of MMPs in keratoconic tissues (Zhou et al., *Invest. Opthalmol. Vis. Sci.* 39:1117–1124, 1998, incorporated herein by reference). The results obtained from these studies reportedly showed that basal levels of gelatin and casein digesting activities were present in healthy human corneas, and that these activities were increased in keratoconus. Gelatin and casein are preferred substrates for gelatinases A and B, and stromelysin. They can, however, also serve as substrates for other proteases.

To determine whether gelatinolytic and caseinolytic activities associated with keratoconus are caused by MMPs or other classes of proteases, Zhou and coworkers (1998, supra) also employed inhibitors specific for four classes of proteases (aspartic, serine, cysteine, and metallo-proteases) as blocking reagents. These studies reportedly showed that, in both healthy controls and keratoconic specimens, the net gelatinolytic and caseinolytic activities were related mostly to serine and cysteine proteases, and not to aspartic proteases, gelatinases A and B, or stromelysin. The inhibitor of serine proteases phenylmethyl sulfonyl fluoride, the cysteine protease inhibitor E-64, and the cathepsin B-trypsin inhibitor leupeptin substantially reduced digestion of gelatin and casein, whereas the aspartic protease inhibitor pepstatin and the MMP inhibitor 1, 10-phenanthroline failed to block the reaction.

These in situ zymographic results may be contrasted with earlier organ culture and cell culture studies which suggested that increased gelatinase activities in keratoconus are caused by gelatinases A and B and stromelysin (Kat et al., *Biochem. Biophys. Res. Commun.* 107:929–36, 1982; Fini et al., *Curr. Eye Res.* 11:849–62, 1992; Ihalainen et al., *Eur. J. Clin. Invest.* 16:78–84, 1986; and Brown et al., *Curr. Eye Res.* 12: 571–8, 1993, each incorporated herein by reference). This model, which previously enjoyed wide acceptance in the keratoconus field, is rejected by Zhou and coworkers, partly on the proposed basis that MMPs may not be present in the cornea in active forms under nonpathologic conditions. In accordance with this model, Zhou and coworkers suggest that most gelatinolytic and caseinolytic activities in healthy human corneas may not be caused by MMPs. Instead, cysteine proteases, such as cathepsin B, and serine proteases, such as cathepsin G, both of which are reportedly elevated in keratoconus, are proposed to contribute to the enhanced gelatin- and casein-digesting activities associated with keratoconus.

Yet other models have been presented to explain the net increase of gelatinase activity in corneas with keratoconus. For example, Sawaguchi and coworkers (*Invest. Ophthalmol. Vis. Sci.* 35:4008–4014, 1994, incorporated herein by reference) propose that this increase may be attributable to decreased levels of tissue inhibitors of metalloprotease (TIMPs) (citing Brown et al., *Curr. Eye Res.* 12:571–581, 1993, incorporated herein by reference) and a2-macroglobulin (citing Bouaboula et al., *J. Biol. Chem.* 267:21830–21838, 1992, incorporated herein by reference). Evidence presented in these and other reports suggests that certain protease inhibitors are reduced in association with keratoconic disease. For example, a decrease in al-protease inhibitor levels were reported in both the epithelial and the stromal layers of keratoconus corneas based on immunostaining and dot blot assays (Sawaguchi et al., *Exp. Eye. Res.* 50:549–554, 1990, incorporated herein by reference). However, when these results were supplemented by computerized colorimetry, it was found that the abnormal inhibitor levels in the stromal layer was confined to the stromal lamellae, and no reduction in the inhibitor level actually occurred in the keratoconus stromal cells. Other evidence based on measurements of mRNA levels suggest that the α1-protease inhibitor may be downregulated in association with keratoconus (Whitelock et al., *Invest. Opthalmol. Vis. Sci.* 38:529–534, 1997, incorporated herein by reference).

Despite the uncertainties apparent from these reports, a number of patent disclosures purport to teach methods for treating corneal disease using protease inhibitors. Specifically, each of the following patents, U.S. Pat. No. 5,962,481, issued Oct. 5, 1999 to Levin et al., U.S. Pat. No. 5,929,097, issued Jul. 27, 1999 to Levin et al., U.S. Pat. No. 5,773,438, issued Jun. 30, 1998 to Levy et al., and U.S. Pat. No. 5,892,112, issued Apr. 6, 1999 to Levy et al., state that synthetic, small molecule, non-peptide protease inhibitors may be useful in treating keratoconus. However, these disclosures add nothing to the foregoing reports with respect to identifying the actual mechanisms that underlie keratoconus, or to clearly elucidate potential treatment agents and modalities for clinical use against the disease. Moreover, each of these disclosures proposes that vast numbers of synthetic protease inhibitors may be used to treat a laundry list of diseases. Thus, both of the Levin et al. patents identify hundreds of synthetic protease inhibitors and generally assert that the disclosed compounds can be used to treat such diverse diseases and conditions as arthritis, tumor growth and metastasis, angiogenesis, tissue ulceration, abnormal wound healing, periodontal disease, bone disease, proteinuria, aneurysmal aortic disease, degenerative cartilage loss following traumatic joint injury, demyelinating diseases of the nervous system, graft rejection, cachexia, anorexia, inflammation, fever, insulin resistance, septic shock, congestive heart failure, inflammatory disease of the central nervous system, inflammatory bowel disease, HIV infection, age related macular degeneration, diabetic retinopathy, proliferative vitreoretinopathy, retinopathy of prematurity, ocular inflammation, keratoconus, Sjogren's syndrome, myopia, ocular tumor, ocular angiogenesis/neovascularization. Most notably, none of the foregoing patents directed toward production and use of small molecule protease inhibitors for disease treatment provide specific direction or guidance as to the underlying mechanisms of keratoconus and other corneal diseases, nor to the preparation and use of effective agents and formulations for treating these diseases.

Further discussion regarding the possible roles of proteases and their inhibitors in keratoconus is also provided by Kenney et al. (*Biochem. Biophys. Res. Comm.* 161:353–357, 1989, incorporated herein by reference). This report focuses on a specific gelatinase, type IV collagenase, which shows marked preference for gelatin (denatured collagen), types IV, V, and VII collagen, and fibronectin as substrates. Notably, the corresponding progelatinase molecule demonstrates considerable amino acid similarity to human procollagenase and prostromelysin. However, regulation of these enzymes is independent, as indicated by studies demonstrating selective increases in progelatinase synthesis accompanied by decreased procollagenase production in response to transforming growth factor-β (Overall et al., *J. Biol. Chem.* 264:1860–1869, 1989, incorporated herein by reference). Also, unlike collagenase and stromelysin, levels of gelatinase expression are not enhanced by exposure of cells to tumor promoter 12-0-tetradecanolyphorbol 13-acetate, but are increased by transformation with H-ras oncogene and treatment with transforming growth factor-β.

Kenney and coworkers report a qualitative disparity between normal and keratoconic tissue samples with regard to this gelatinase. Normal keratocyte culture media contains a greater quantity of this gelatinase than media from keratoconus cultures. However, the keratoconus media displays increased gelatinolytic activity. Further characterization showed that the gelatinolytic activity is inactivated by chelators, dithiothreitol (DTT) and B-mercaptoethanol but is not effected by 1mM phenylmethanesulfonyl fluoride (PMSF).

Based on these results, Kenney et al. propose an alternative mechanism to the protease/protease inhibitor imbalance model proposed by others. In particular, the authors suggest that there may be an inherent difference between the diseased and normal gelatinase enzyme, for example due to post-transnational modifications, amino acid differences leading to increased susceptibility to activation, or other factors. This proposal is in general agreement with a model advanced by Rehaney et al., who suggest that there is a high level of collagenase in an active form in keratoconic corneas, without trypsin activation, whereas the corresponding enzyme(s) in normal corneas is present in a latent form (*Ann. Opthalmol.* 14:751–754, 1982, incorporated herein by reference).

Other studies directed toward identifying protein degradative mechanisms in keratoconus have focused on lysosomal enzyme abnormalities associated with the disease. Lysosomal enzymes are widely distributed in ocular tissues, including the cornea, and have been implicated in several ocular diseases, such as uveitis and retinal degeneration. In addition to these pathogenic associations, Sawaguchi et al. reported that corneas from patients with keratoconus exhibited elevated levels of three acid hydrolases when compared with normal human corneas (*Arch. Opthalmol.* 107:1507–1510, 1989, incorporated herein by reference). This elevation was most prominently seen with acid phosphatase and was highlighted in the basal epithelium of keratoconus specimens.

Lysosomal enzymes are active elements participating in the degradation of protein, polysaccharide, nucleic acids, and lipids into low-molecular-weight constituents under acidic pH. They are also involved, physiologically, in phagocytosis and catabolism, and, pathologically, in inflammation, immune responses, and lysosomal storage diseases. The finding that corneas with keratoconus contain higher-than-normal levels of lysosomal hydrolases thus provides yet another candidate for a molecular/biochemical determinant in keratoconus. However, further investigation is also required to determine whether this abnormality represents a primary, or incidental, factor in keratoconus disease development. Underscoring this point, Sawaguchi and colleagues reported significant heterogeneity in lysosomal enzyme levels among keratoconus specimens analyzed in their study. These variations could not be correlated to differences in medical histories, clinical features, or histopathologic characteristics, such as degree of scarring or keratometric readings, again pointing to a heterogeneous pathology for the disease.

Thus, as in the case of other postulated determinants of keratoconus, no conclusive evidence has emerged to implicate changes in ECM protein structure, expression, and/or degradative metabolism as pathogenetic causes in the disease. Reported changes in protease and protease inhibitor properties (e.g., expression, structure, activity or metabolism) are difficult to interpret, and to reconcile with other reports. Thus, it is unclear whether these changes may contribute to onset or progression of keratoconus, or merely represent incidental sequelae of the disease. Resolution of these alternative possibilities is further complicated by the possibility that protease and protease inhibitor activities may be altered in keratoconus as a result of concurrent wound-healing and repair mechanisms, allergic responses, or responses to mechanical trauma, rather than as a direct effect of the primary disease. For example, declines in the protease inhibitor levels in the cornea may simply be a reflection of a similar decline in tears, or in serum. It has been shown that hormonal balance (Findlay et al., *Endocrinology* 108:2129–2135, 1981) and allergic disease (Berman et al., *Invest. Opthalmol. Vis. Sci.* 12:759–770, 1973, each incorporated herein by reference) can affect protease inhibitor levels in tears and in serum, and allergic diseases are often associated with keratoconus (Rahi et al., *J. Opthalmol.* 61:761–764, 1977, incorporated herein by reference).

Still other biochemical and molecular mechanisms have been postulated to play a determinative role in the onset and progression of keratoconus. In particular, detailed studies concerning the role of extracellular matrix materials (ECMS) in keratoconus have focused on aberrant macromolecular and biochemical properties of native proteoglycans. The mechanical strength of the corneal collagen-fiber network depends not only on the formation of covalent cross-links between collagen molecules, but also on a precise interaction of collagen with matrix proteoglycans. These interactions stabilize the collagen network and maintain regular spacing of the collagen fibers. Thus, even minor deviations in the structure of proteoglycans may impair the stabilizing effect of proteoglycans on the collagen network, resulting in increased distensibility of the corneal tissue over time (Edmund, *Acta. Ophthalmol.* 65:545–550, 1987, incorporated herein by reference). This proposed mechanism is consistent with the slowly progressive development of keratoconus which often requires several years for full expression.

Consistent with the above noted histologic and ultrastructural findings, keratoconic corneas have been shown to exhibit abnormal accumulations of chondroitin- and dermatan sulfate-type proteoglycans around collagen fibrils and collagen lamellae (Sawaguchi et al., *Invest. Ophthalmol. Vis. Sci.* 32:1846–1853, 1991, incorporated herein by reference). In addition, numerous pores noted in the stroma of keratoconic corneas are thought to represent areas occupied by keratocytes and abnormal proteoglycan molecules (Sawaguchi et al., *Arch. Ophthalmol.* 116:62–68, 1998, incorporated herein by reference). These and other findings point to an association between keratoconic structural defects and aberrant properties of proteoglycans in the corneal matrix.

In one study directed to the role of ECM proteoglycans in keratoconus, Budeecke and Wollensak isolated ECM components from metabolically labeled, normal and keratoconic, human corneas (*Graefe's Arch. Clin. Exp. Ophthalmol.* 171:105–120, 1966, incorporated herein by reference). These studies revealed a significant increase in hexosamine content in the keratoconic cornea. No change was observed in the ratio of chondroitin sulfate/keratan sulfate (CS/KS) in keratoconic compared to normal corneas. Analysis of the overall mass and relative molecular mass ($M_r$) of the protein core and the glycosaminoglycan side chains of proteochondroitin sulfate (CS-PG) dermatan sulfate proteoglycan (DS-PG) and keratan sulfate-containing proteoglycan (KS-PG) revealed differences between normal and keratoconic cornea in the ratio of DS-PG/KS-PG, and in the chain length of KS chains. The latter finding suggests a higher proportion of KS-PG molecules having a lower than normal molecular weight, corresponding to a reduction of about 40% in the length of KS chains, in keratoconic compared to normal corneas.

Further suggesting a causal role for extracellular matrix glycoproteins in keratoconus are reports documenting marked increases in uronic acid, neutral hexoses, and N-acetylgalactosamine as well as elevated amounts of corneal glycoconjugates in keratoconus extracts compared to normal controls (Critchfield et al., *Exp. Eye Res.* 34:83–98, 1982; Yue et al., *Arch. Ophthalmol.* 106:1709–1712, 1988, each incorporated herein by reference). Based on these and other reports, researchers have proposed that the structure, composition and/or levels of ECM glycoproteins in the cornea may be important determinants of the onset and progression of keratoconus.

The role of proteoglycan structure and metabolism in keratoconus may be influenced by a variety of complex molecular and biochemical factors. In this context, recent discussion has been directed toward specific proteases as potential modulators of proteoglycan structure/metabolism. Cathepsin B, a cysteine protease, and cathepsin G, a neutral serine protease, are both enzymes known to degrade proteoglycans in the corneal stroma, which is the site of thinning and scarring in keratoconus. Both are synthesized as large-molecular weight precursors containing signal- and pro-sequences that undergo several post-transcriptional modifications before being targeted to lysosomes and possibly other compartments of the endocytic or secretory pathways (Wang et al., *J. Biol. Chem.* 266:12633–12638, 1991, incorporated herein by reference). In human colorectal carcinoma, (Jessup et al., *Am. J. Pathol.* 145:1–11, 1994, incorporated herein by reference) and during fetal calf myoblast-myotube differentiation, (Bechet et al., *J. Biol. Chem.* 266:14104–14112, 1991, incorporated herein by reference), the activity of cathepsin B has been shown to be increased due to induction of cathepsin gene transcription, alteration in the secretion pathway, or modification of enzyme properties. The increased cathepsin B and G activities in keratoconus also may be related to increased gene transcription (Whitelock et al., *Invest. Ophthalmol. Vis. Sci.* 38:529–534, 1997, incorporated herein by reference). However, at present, the exact mechanisms by which cathepsin expression is controlled in the cornea under nonpathologic conditions, and how those conditions are altered in association with keratoconus, remain poorly understood.

Although the foregoing models embrace much of the current knowledge pertaining to biochemical and molecular mechanisms in keratoconus, new models for this disease continue to emerge. One such model focuses on aberrant epithelial-stromal interactions, which are thought to comprise a fumdamental aspect of disease development in keratoconus. In this regard, Wilson and colleagues have postulated that interleukin 1 (IL-1) may be a cytokine modulator of epithelial-stromal interactions, regulating corneal cell proliferation, differentiation, and cell death (*Exp. Eye Res.* 62:325–337, 1996, incorporated herein by reference). These investigators have also proposed a causal role of the IL-1 system in keratoconus. Support for this model includes findings that cultured keratoconus stromal cells contain 4-fold higher binding sites for IL-1 (Fabre et al., *Curr. Eye Res.* 7:585–592, 1991, incorporated herein by reference). Also noteworthy are studies which show enhanced expression of the IL-1 receptor associated with keratoconus. Zhou et al., *Invest. Ophthalmol. Vis. Sci.* 37(suppl):S1017, 1996, incorporated herein by reference. The hypothesis that IL-1 plays a causal role in keratoconus is also consistent with a model of corneal degradation mediated by matrix metalloproteases, because IL-1 is known to regulate the expression of MMPs in the cornea. Girard et al., *Invest. Ophthalmol. Vis. Sci.* 32:2441–2454, 1991, incorporated herein by reference.

Considering all of the above reports in their entirety, it is clear that the etiology of keratoconus remains uncertain. Whereas the gross anatomical, histological, and ultrastructural defects associated with keratoconus clearly represent proximate causes of the disease, the underlying biochemical and molecular mechanisms that trigger the onset and progression of these defects remain unclear and open to much debate. Most importantly, despite extensive efforts in the clinic and laboratory to model the disease and develop preventive and therapeutic tools, management of keratoconus generally remains limited to physical intervention by corrective lenses and transplantation surgery.

Information that is available concerning the ultimate, biochemical and molecular causes of keratoconus provides limited promise of future treatments or cures for the disease. In this context, the reports summarized above present complex and often conflicting etiologic models. Even simple genetic models for the disease are complicated by, or conflict with, models that embrace mechanical factors (e.g., eye rubbing or contact lens wear) as causes for the disease. Yet additional environmental causes, including atopic disease and systemic conditions, further complicate etiological modeling of the disease and support a heterogenous pathology attributable to a number of causes that can lead independently to common symptoms (see, e.g., Yue et al., *Proc. Soc. Exp. Biol. Med.* 175:336–341, 1984, incorporated herein by reference).

Although particular interest has been directed to ultrastructural defects in keratoconus (fragmentation of Bowman's layer and epithelial basement membrane, and fibrillation of anterior stroma), no definitive mechanisms have been resolved to account for these changes. However, much attention has been directed to the extracellular Bowman's layer, which resides at a dynamic interface between the corneal epithelium and stroma. Components of Bowman's layer are thought to be synthesized by both corneal epithelial and stromal cells, and maintenance of this layer is believed to require complex epithelial-stromal interactions.

As noted above, it has been widely proposed that changes in the metabolism and/or composition of extracellular matrix materials (ECMs) are responsible for the observed defects in Bowman's layer and other structural changes associated with keratoconus. However, the number and diversity of ECM components postulated to play a role in this context are extensive, and the complexity of proposed structural and metabolic interactions among these components is commensurately difficult to resolve.

Briefly summarizing the possible roles of ECM components in keratoconus, a large number of studies have focused on the role of collagen maintenance in the cornea. In this context, it has been proposed that the collagen maintenance function of stromal cells and/or cytokines may be disturbed for both Bowman's layer and for the stroma. However, the organization and maintenance of collagens in Bowman's layer remains unexplained.

Some studies that have examined the role of collagen maintenance in the cornea report no differences in spatial distribution and specific immunostaining, nor in amino acid composition and cross-linkages of collagens, between keratoconic and normal tissues. Other studies report abnormal, loosely packed and randomly oriented collagen fibrils in the corneal stroma of some keratoconus patients. Yet additional studies conclude that collagen content is increased, while others report a reduction in collagen content associated with keratoconus.

Further complicating the prospective etiology of keratoconus are reported changes in the proteoglycan content and metabolism that attend this disease. In particular, keratoconic corneas exhibit abnormal accumulations of chondroitin- and dermatan sulfate-type proteoglycans around collagen fibrils and collagen lamellae. In addition, there is a significant increase in hexosamine content in keratoconic corneas. Of particular note are changes in the ratio of dermatan sulfate proteoglycan (DS-PG) and keratan sulfate-containing proteoglycan (KS-PG) between normal and keratoconic corneas, as well as alterations in the length of KS chains. Further suggesting a causal role for extracellular matrix glycoproteins in keratoconus are noted increases in uronic acid, neutral hexoses, and N-acetylgalactosamine as well as elevated amounts of corneal glycoconjugates associated with the disease In summary, reports of altered protein and glycoprotein levels and metabolism in keratoconus have prompted researchers to speculate on numerous possible mechanisms that may underlie the disease. These postulated mechanisms variously involve one or more proposed alterations in the levels, structure, expression and/or metabolism of extracellular proteins and/or proteoglycans. These alterations may be independent from, or coupled with, changes in the levels, structure, expression and/or activity of degradative enzymes, which are in turn variously proposed to be independent from, or associated with, alterations in the levels, structure, expression and/or activity of enzyme inhibitors. As discussed in detail above, all of these proposed mechanisms remain unresolved with respect to their causal, or incidental, roles in the pathogenic processes of keratoconus.

In view of the foregoing, the underlying biochemical and molecular mechanisms that control the onset and progression of keratoconus have heretofore remained unclarified. Thus, prior to the instant invention, an adequate platform from which to begin developing effective tools to treat or prevent this disease has remained out of reach.

It is therefore an object of the invention to provide effective therapeutic methods and compositions to treat and prevent keratoconus and other corneal disorders sharing common etiological characteristics of aberrantly high proteolytic activity with keratoconus. Included among these additional disorders are pathogenic infections, ulcers, and responses to injury attended by aberrant proteolytic activity.

It is a fuirther object of the invention to achieve the foregoing objects within methods and compositions that are easy to administer and which employ formulations that optimize delivery of therapeutic agents to ocular target sites including extracorneal fluid (tears, aqueous humor, or vitreous humor), corneal tissues, and vitreous humor.

Consistent with the foregoing objects, it is an additional object of the invention to provide methods and compositions that minimize discomfort and other adverse sequelae (e.g., corneal trauma, chemical irritation, visual impairment, etc.) associated with the foregoing treatment methods and compositions.

It is yet another object of the invention to provide the foregoing treatment methods and compositions in a combinatorial manner with other therapeutic methods and agents, to alleviate keratoconus concurrently with other, secondary ocular disorders. Targeted secondary disorders in this context include, but are not limited to, pathogenic infection, eye discomfort or irritation, atopic disease, and visual impairment. In more detailed aspects, methods and compositions for treating keratoconus are adapted for combinatorial use with corrective contact lenses, including rigid gas-permeable (RGP) lenses.

SUMMARY OF THE INVENTION

The invention fulfills these objects and satisfies other objects and advantages by providing novel methods and compositions for the treatment or prevention of corneal disease in a mammalian patient.

The methods of the invention involve ocular administration of an antiproteolytic effective amount of a protease inhibitor in an opthalmically acceptable carrier. The protease inhibitor is preferably a protein or peptide protease inhibitor selected from an aspartic, serine, cysteine, or metalloprotease inhibitor, which may be derived from a natural source or produced in a native or modified form by recombinant or synthetic techniques known in the art. In most instances, recombinant or synthetic protease inhibitors are preferred, as these materials will generally be free of undesirable contaminants and infectious agents.

According to the methods of the invention, a protease inhibitor formulation is administered to an ocular fluid, surface, or tissue, preferably by topical administration, in an antiproteolytic effective amount to substantially inhibit a proteolytic activity associated with the corneal disease or condition to be treated. Proteolytic activities in this context may include activities of multispecific or specific proteases, complex formation between a protease and protease inhibitor, histopathological changes in the cornea attributed to proteolytic processes, and other indicia correlated with proteolytic mechanisms.

The antiproteolytic formulations of the invention can include various carriers that prolong retention and/or enhance delivery of the inhibitor. Optionally, the antiproteolytic formulations can include permeabilizing agents and preservatives, which may be a single agent that enhances permeability and provides a simultaneous preservative function. In addition, the formulation can include a plurality of protease inhibitors, as well as other therapeutic agents such as antiinflammatory or antibiotic drugs.

Mode, timing, and duration of treatment according to the methods of the invention vary in accordance with a variety of factors detailed below. In preferred aspects of the invention, antiproteolytic formulations are administered during periods when contact lens are worn and/or of closed eye tear production to enhance therapeutic efficacy.

Also provided within the invention are implant devices adapted for corneal delivery of an effective amount of an antiprotease. These devices are provided in the form of an ocular implant having a concave inner surface similar in size and shape to the inner surface of a contact lens. The device is applied externally to the cornea of a patient suffering from a corneal disease or condition and serves as a carrier to deliver to the cornea an antiproteolytically effective amount of a protease inhibitor.

DESCRIPTION OF THE SPECIFIC EMBODIMENTS

The instant invention provides useful methods and compositions for treating or preventing corneal disease in a mammalian patient. The methods of the invention involve ocular administration of an antiproteolytic effective amount of a protease inhibitor in an opthalmically acceptable carrier. The protease inhibitor is preferably selected from an aspartic, serine, cysteine, or metallo-protease inhibitor, obtained from a natural source or produced in a native (i.e., wild-type amino acid sequence) or modified (e.g., by amino acid substitution, insertion, deletion, truncation or extension, or by activation, fusion or conjugation with other proteins or chemical moieties) by recombinant or synthetic techniques known in the art.

According to the methods of the invention, a protease inhibitor formulation is administered to an ocular fluid, surface, or tissue, preferably by topical administration, in an antiproteolytic amount effective to substantially inhibit a proteolytic activity associated with the corneal disease or condition to be treated.

By substantial inhibition of proteolytic activity is meant that administration of the protease inhibitor formulation yields at least about a 10% reduction of proteolytic activity, preferably at least a 20% reduction, compared to a relevant baseline or control value at an ocular target site, for example within the extracorneal fluid, corneal epithelium, corneal stroma, Bowman's layer, or the vitreous humor. Preferably, administration of the protease inhibitor yields approximately a 30–50% reduction of proteolytic activity, more preferably greater than about a 50% reduction, and in some preferred aspects yields effective neutralization of proteolytic activity in a treated sample corresponding to a reduction of between approximately 85% and 100% of the proteolytic activity measured for the relevant baseline or control sample.

As used herein, proteolytic activity refers to a quantitative digestive activity of a target protease against a protein (e.g., collagen, elastin, fibronectin) or glycoprotein (e.g., a proteoglycan or glycosaminoglycan) substrate. Target proteases as herein defined include proteolytic enzymes that exhibit aberrantly high levels of expression or activity (e.g., attributable to structural changes that increase substrate binding or otherwise enhance digestion kinetics, or that render the protease more susceptible to activation from a proenzyme to an active form), or whose regulation (e.g., by metabolic turnover, protease inhibition or other mechanisms) is impaired in association with a corneal disease or condition to be treated, for example keratoconus or corneal infections. As further defined herein, target proteases are amenable to regulatory inhibition by exogenously administered protease inhibitors.

Proteases that may be successfully targeted for inhibition by the compositions and methods of the invention include, but are not limited to, acid esterases, acid phosphatases, acid lipases, cathepsins (e.g., cathepsin B and G), collagenases, elastases, tryptases, chymases, kinins, kalikreins, tumor necrosis factors, chymotrypsins, stromelysins, and matrix metalloproteases (e.g., gelatinase A or MMP-2, gelatinase B or MMP9, MMP1, MMP 8, and MMP 13).

Antiproteolytic activity may be determined by, e.g., various quantitative, in vitro or in vivo assays, for example by enzymatic and/or immunological assays using extracorneal fluid samples, samples from keratocyte culture media, or corneal tissue samples, as described herein below and as otherwise known in the art. Alternatively, antiproteolytic activity may be determined by other indicia, for example by quantitative changes in morphological or ultrastructural features attributable to proteolytic activity that are amenable to prevention or inhibition using the compositions and methods of the invention. Exemplary indicia in this context include quantitative changes in the extent of fragmentation of Bowman's layer, fragmentation of the epithelial cell basement membrane, and/or fibrillation of the anterior corneal stroma. These indicia can be readily compared between treated samples and relevant control samples, for example by histopathological computer-aided image analysis that resolves percentages of optical field areas occupied by proteolytically altered versus normal histological structures (e.g, fragmented versus non-fragmented areas of Bowman's layer).

The extent of antiproteolytic activity elicited by the compositions and methods of the invention (i.e., for determining efficacy and calibrating dosages) can be determined by a variety of assays that compare relevant test and control samples, as detailed in the examples below. Suitable in vitro test and control samples include cultured, normal and keratoconic keratocytes, respectively, each treated with an antiprotease formulation of the invention. Using these samples, protease inhibition can be measured at selected time points, for example, by assaying target protease-inhibitor complex formation, rates or levels of protein digestion attributed to the target protease, morphological indicia as noted above, and other parameters consistent with the quantitative values sought.

Alternate quantitative inhibition assays can be conducted using, e.g., cultured keratocytes or corneal tissues taken from subjects with keratoconic and normal corneas to provide, respectively, test and control samples for in vitro assays. For quantitative determination of in vivo protease inhibition, test and control samples may include extracorneal fluid or corneal tissue samples taken from subjects (e.g., a human or non-human mammal such as a rabbit) following administration of a protease inhibitor formulation (test sample), and following administration of a placebo comprising, e.g., a selected carrier without the protease inhibitor (control sample). Often, test and control samples will be provided by bilateral administration of test and control treatments to an individual patient. Other suitable test and control samples will be determined by those skilled in the art according to the objectives and methods of the chosen assay, as exemplified herein below.

Protease inhibitors that are useful within the invention are any of the inhibitors, their analogs, recombinantly modified variants, proteolytically active fragments, derivatives, or salts, which can inhibit target proteases as defined above. Preferably, the inhibitor is a protein or peptide of sufficient molecular size for use within the formulations described herein that provide for enhanced absorption, retention and delivery of the inhibitor at a site of treatment. In various preferred embodiments, the protease inhibitor may be selected from an aspartic, serine, cysteine, or metalloprotease inhibitor. Useful inhibitors may be derived from a natural source or produced in a native or modified form by recombinant or synthetic techniques known in the art. In more detailed aspects of the invention, protease inhibitors bind with one or more proteases that exhibit increased levels of expression or activity, or aberrant regulation, leading to pathogenic protein or glycoprotein degradation and/or morphologic changes associated with a corneal disease or condition to be treated.

As noted above, preferred protease inhibitors include native or modified aspartic, serine, cysteine, or metalloprotease inhibitors. Exemplary inhibitors in this context include α1-antiprotease (alp1, formerly known as α1-antitrypsin), α2-macroglobulin (α2-M), secretory leucocyte protease inhibitor (SLP1, formerly known as mucus proteinase inhibitor and antileukoprotease), β1-antigellagenase, α2-antiplasmin, serine amylyoid A protein, al -antichymotrypsin (α1-Achy), cystatin C, inter-α-trypsin inhibitor, elafm, elastinal, aprotinin, phenylmethyl sulfonyl fluoride, the cysteine protease inhibitor E-64, the cathepsin B-trypsin inhibitor leupeptin, and the metalloprotease inhibitors TIMP-1, TIMP-2, and 1, 10-phenanthroline.

A particularly preferred protease inhibitor for use within the compositions and methods of the invention is α2-macroglobulin. This inhibitor is a high-molecular-weight (718 kD), homotetrameric glycoprotein implicated as a regulator of degradation for certain extracellular matrix components and other macromolecules. Unlike many other protease inhibitors, α2-macroglobulin is not highly specific for a preferred target protease, and is not particularly fast acting. Instead, α2-macroglobulin inhibits proteases from all four major classes and is considered to be relatively slow in its activity. Consistent with these properties, the mechanism of action by α2-macroglobulin is also unique. When this protease inhibitor reacts with a target protease, proteolytic cleavage in the "bait region" of the inhibitor occurs, leading to a conformational change and trapping of the protease. A covalent bond is then formed between the protease and α2-macroglobulin. The protease-inhibitor complex is ultimately cleared from the circulation by a receptor-mediated mechanism.

Another preferred protease inhibitor for use within the compositions and methods of the invention is α-1 protease inhibitor (alp1), a major protease inhibitor in human plasma synthesized mainly by parenchymal liver cells. Alp1 is a glycoprotein of 53 kDa that forms a 1:1 complex with its target enzyme, leukocyte elastase. In addition to this primary target, alp1 inhibitor also inhibits chymotrypsin, cathepsin G, trypsin, plasmin, and thrombin. It is present in most body fluids, as well as in many tissues and cells. Alp1 has been demonstrated in all three layers of normal cornea as well as in the tears and aqueous humor.

As noted above, useful compositions within the invention include formulations of antiprotease salts, derivatives and complexes. As used herein, the term pharmaceutically acceptable salts, derivatives and complexes retain the desired biological activity of the corresponding native antiprotease, and exhibit minimal undesired toxicological effects. Nonlimiting examples of useful antiprotease salts are acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalacturonic acid; base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylene-diamine, Dglucosamine, ammonium, tetraethylammonium, or ethylenediamine; or combinations of acid and base addition salts.

Pharmaceutically acceptable derivatives and complexes of protease inhibitors include native or modified inhibitors that are chemically modified (e.g., by addition of stabilizing or otherwise finctional chemical moieties), truncated, conjugated (e.g., to a second protein, peptide or carrier) or recombinantly modified (e.g. by site directed mutagenesis using a cDNA encoding the inhibitor to introduce substitute, or delete non-critical amino acid residues), which retain desired biological activity of the corresponding native antiprotease.

Particularly useful in this context are protease inhibitor analogs, which comprise recombinantly modified variants and proteolytically active fragments of native inhibitors. These analogs preferably exhibit at least 80% amino acid identity, more preferably 95% or greater amino acid similarity, as compared to the amino acid sequence of the corresponding native inhibitor, as determined by conventional sequence alignment and comparison methods.

Alignment of amino acid sequences and calculation of percent identity between the aligned sequences is routine in the art. Such routine alignments include the introduction of gaps and employ other widely known conventions to account for sequence additions, deletions, conservative substitutions, etc. Briefly, conventional sequence comparison methods involve alignment of the compared sequences to yield the highest possible alignment score, which is readily calculated according to well known methods based on the number of amino acid or nucleotide matches.

Antiprotease analogs preferably share substantial amino acid sequence identity (e.g., at least 75%, preferably 80%, and more preferably 95% or greater sequence identity) with a "reference sequence" of a corresponding native inhibitor protein or active polypeptide fragment thereof. As used herein, this reference sequence is a defined sequence used as a basis for a sequence comparison. Generally, a reference sequence is at least 20 amino acid residues in length, frequently at least 25 amino acid residues in length, and often at least 50 amino acid residues in length. Since analog and native fragment polypeptides may each (1) comprise a sequence (ie., a portion of the complete native sequence) that is similar between the two polypeptides, and (2) may further comprise a sequence that is divergent between the two polypeptides, sequence comparisons between two (or more) polypeptides are typically performed by comparing sequences of the two polypeptides over a "comparison window" to identify and compare local regions of sequence similarity. A "comparison window", as used herein, refers to a conceptual segment of at least 20 contiguous amino acid residues wherein a polypeptide sequence may be compared to a reference sequence of at least 20 contiguous amino acid residues and wherein the portion of the polypeptide sequence in the comparison window may comprise additions or deletions (i.e., gaps) of 20 percent or less as compared to the reference sequence (which does not comprise additions or deletions) for optimal alignment of the two sequences.

Optimal alignment of sequences for aligning a comparison window may be conducted by the local homology algorithm of Smith & Waterman, (*Adv. Appl. Math.* 2:482, 1981, incorporated herein by reference), by the homology alignment algorithm of Needleman & Wunsch, (*J. Mol. Biol.* 48:443, 1970, incorporated herein by reference), by the search for similarity method of Pearson & Lipman, (*Proc. Natl. Acad. Sci. USA* 85:2444, 1988, incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis., incorporated herein by reference), or by inspection, and the best alignment (i.e., resulting in the highest percentage of sequence similarity over the comparison window) generated by the various methods is selected. The term "sequence identity" means that two polypeptide sequences are identical (i.e., on an amino acid-by-amino acid) over the window of comparison. The term "percentage of sequence identity" is calculated by comparing two optimally aligned sequences over the window of comparison, determining the number of positions at which the identical amino acid residues occur in both sequences to yield the number of matched positions, dividing the number of matched positions by the total number of positions in the window of comparison (ie., the window size), and multiplying the result by 100 to yield the percentage of sequence identity. The terms "substantial identity" as used herein denotes a characteristic of a polypeptide sequence, wherein the polypeptide comprises a sequence that has at least 80 percent sequence identity, preferably at least 95 percent sequence identity, more usually at least 99 percent sequence identity as compared to a reference sequence over a comparison window of at least 20 amino acid residues, frequently over a window of at least 25–50 amino acid residues, wherein the percentage of sequence identity is calculated by comparing the reference sequence to the analog sequence which may include modifications (e.g., deletions, substitutions, or additions) which total 20 percent or less of the reference sequence over the window of comparison. The reference sequence may be a subset of a larger sequence.

In addition to these polypeptide sequence relationships, protein analogs and peptide fragments of the invention are also typically selected to have conservative relationships with corresponding, native reference proteins and polypeptides. Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. Abbreviations for the twenty naturally occurring amino acids used herein follow conventional usage (Immunology—A Synthesis (2nd ed., E. S. Golub & D. R. Gren, eds., Sinauer Associates, Sunderland, Mass., 1991), incorporated herein by reference). Stereoisomers (e.g., D-amino acids) of the twenty conventional amino acids, unnatural amino acids such as $\alpha,\alpha$-disubstituted amino acids, N-alkyl amino acids, lactic acid, and other unconventional amino acids may also be suitable components for polypeptides of the present invention. Examples of unconventional amino acids include: 4-hydroxyproline, $\gamma$-carboxyglutamate, $\epsilon$-N,N,N-trimethyllysine, $\epsilon$-N-acetyllysine, O-phosphoserine, N-acetylserine, N-formylmethionine, 3-methylhistidine, 5-hydroxylysine, $\omega$-N-methylarginine, and other similar amino acids and imino acids (e.g., 4-hydroxyproline). Moreover, amino acids may be modified by glycosylation, phosphorylation and the like.

For practicing the methods of the invention, the precise amounts of protease inhibitors to be administered and the frequency and duration of treatment will depend on the status of the corneal condition or disease to be treated, and on other factors such as the patient's state of health and weight, the mode of administration, the nature of the formulation, etc. These factors will vary such that specific regimens can be established by those skilled in the art to maximize efficacy of treatment. Ordinarily, the antiprotease is administered in a dosage of between approximately 0.2 $\mu$g/ml and 1.0 mg/ml. Preferably, the inhibitor is present in a concentration of about 0.1–1.0 $\mu$g/ml, more preferably at a concentration of about 0.5 $\mu$g/ml. Exemplary formulations for $\alpha$1-antitrypsin will comprise the inhibitor at approximately the same range of concentrations, with the most preferred concentration being between about 1.0 and 5.0 $\mu$g/ml. The administration schedule can range from a continuous infusion, to once or twice a day, up to 6 or more administrations a day, with dose levels and administration protocols being selected by the health professional. Administration onto the concave surface of contact lenses before insertion into the eye is an effective method of enhancing the residence time for the solution in contact with the cornea.

Thus, treatments according to the invention can be in the form of a one time dose, e.g., in the context of sustained delivery and long-term delivery formulations described below. Alternatively, multiple administrations may be indicated and, under certain circumstances, continuous treatments may be selected.

In a preferred aspect of the invention, compositions comprising a protease inhibitor are administered during periods of closed eye tear production (e.g., during a patient's sleep periods). This method greatly enhances antiproteolytic results, yielding prolonged inhibition of proteolytic processes in corneal tissues (e.g., as demonstrated by reduction in the activity of specific target protease(s)), and long-term inhibition of histopathological changes, such as fragmentation of Bowman's layer. Administration of the antiprotease compositions of the invention during periods of closed eye tear production greatly enhances the antiproteolytic efficacy of these compositions compared to the efficacy achieved by antiprotease administration during periods of reflex tear production, although the latter use is effective and within the scope of the invention. This is due in part to the prolonged retention of the antiprotease composition attributable to a reduction in tear flushing between closed eye and reflex tear periods. This enhanced efficacy is also attributable to fundamental differences in the processes and regulation of proteolysis that characterize the closed eye, versus reflex tear environments. The protease inhibitor compositions and pharmaceutical formulations of the invention can also be administered during a period that is concurrent with or closely preceding a medical procedure or other event anticipated to produce a risk of proteolytic injury, for example following eye surgery or during bacterial infection. Thus, methods are provided which involve administration of an antiproteolytic composition concurrent with, or within an antiproteolytic effective period preceding or following, a surgical procedure or infection, whereby the administration reduces or eliminates risk of deleterious proteolytic responses normally associated with the procedure or infection.

Within the methods of the invention, formulations comprising a protease inhibitor, a mixture of a plurality of protease inhibitors, or a mixture of one or more protease inhibitors combined with a second therapeutic agent (e.g., an antibiotic, antiviral or antiinflammatory drug) can be administered by a variety of routes, including via topical administration (using, e.g., drops, gels, creams or microparticles as carriers), injection (e.g., via hypodermic or pneumatic introduction into the cornea or vitreous humor).

Preferred methods of the invention involve coordinate (e.g., simultaneous or closely contemporaneous to yield coordinate treatment) administration of a plurality of antiprotease proteins, analogs, salts, or derivatives, or administration of formulations comprising multiple protease inhibitors that may be admixed or complexed. Practice of these methods reduces abnormal proteolytic mechanisms attending a targeted corneal disorder (e.g., keratoconus) at combinatorial antiproteolytic levels that exceed antiproteolytic levels observed when either of the coordinately administered protease inhibitors are administered alone. This inhibition, as when other compositions and methods of the invention are employed, reduces proteolytic activity in extracorneal fluid (tears), and in corneal tissues (as determined by both enzymatic and histopathological assays). In preferred embodiments, a multispecific protease inhibitor (i.e., an inhibitor which targets multiple protease species), such as α2-M, SLP1 and alp1, is coordinately administered with another multispecific inhibitor, or, alternatively, a multispecific inhibitor is coordinately administered with an oligospecific or specific inhibitor (the latter types of inhibitors represented, e.g., by β1-antigellagenase, α2-antiplasmin, serine amyloid A protein, α1-antichymotrypsin (α1-Achy), cystatin C, inter-a-trypsin inhibitor, elafin, elastinal, aprotinin, phenylmethyl sulfonyl fluoride, leupeptin, and the metalloprotease inhibitors TIMP-1, TIMP-2, and 1, 10-phenanthroline). Using these combinatorial compositions and treatment methods, the invention achieves effective inhibition against multiple proteases (and/or their pathogenic effects) involved in a particular corneal disease process. Thus, the methods and compositions of the invention provide antiproteolytic effects against a broad range of proteases, including but not limited to, acid esterases, acid phosphatases, acid lipases, cathepsins, collagenases, elastases, tryptases, chymases, kinins, kalikreins, tumor necrosis factors, chymotrypsins, stromelysins, and matrix metalloproteases, thereby alleviating or preventing the targeted corneal disease or condition.

Additional preferred methods of the invention involve coordinate administration of an antiprotease and an antibiotic, or administration of formulations comprising both a protease inhibitor and an antibiotic. Practice of these methods reduces abnormal proteolytic mechanisms attending a targeted corneal disorder (e.g., keratoconus) and also secondarily reduces proteolytic effects attributed to bacterial infection. Useful antibiotics may be any opthalmically acceptable antibiotic indicated for treatment of an ocular bacterial infection, including, but not limited to fluoroquinolones (e.g., ofloxacin, norfloxacin, ciprofloxacin), gentamicin, and pilocarpine.

Other medications useful in these combinatorial treatment methods include steroidal antiinflammatories, such as corticosteroids, and nonsteroidal antiinflammatories, for example aspirin, ibuprofen, indomethacin, fenoprofen, mefenamic acid, flufenamic acid, and sulindac. Many other combinatorially effective medicaments useful for coordinate ophthalmic treatment within the methods of the invention will be apparent to the skilled practitioner.

Typically, the protease inhibitors, analogs, salts, derivatives, and coordinately administered therapeutic agents of the invention will be administered in the form of a pharmaceutical composition, ie., dissolved or suspended in a physiologically acceptable carrier, preferably an aqueous carrier. A variety of aqueous carriers may be used, e.g., water, buffered water, 0.4% saline, 0.3% glycine and the like. Many other suitable carriers are known in the art and readily formulated with the subject therapeutic agents, including biologically compatible gels, creams, microparticulate solutions and the like suitable for topical administration. The pharmaceutical compositions may be sterilized by conventional, well known sterilization techniques. The resulting formulations may be packaged for use or filtered under aseptic conditions and lyophilized, the lyophilized preparation being combined with a sterile aqueous solution or other carrier prior to administration.

In other embodiments of the invention, the protease inhibitors, analogs, salts, derivatives, and coordinately administered therapeutic agents of the invention are prepared with carriers that protect the compound against rapid elimination from the ocular environment, such as are routinely used in controlled release devices and formulations (e.g., implants and microencapsulated delivery systems). Biodegradable, biocompatible polymers can be used, such as ethylene vinyl acetate, polyanhydrides, polyglycolic acid, colla-gen, polyorthoesters, and polylactic acid. Such formulations and methods for their preparation will be apparent to those skilled in the art.

In a particularly preferred aspect of the invention, a novel delivery device is provided in the form of an ocular implant adapted for corneal delivery of an effective amount of an antiprotease. The device has a concave inner surface that conforms to an external surface of the cornea, i.e., which is similar in size and shape to the inner surface of a contact lens, and is applied externally to the cornea of a patient suffering from a corneal disease or condition. The device serves as a carrier to deliver to the cornea an antiproteolytically effective amount of a protease inhibitor. Preferably, the device is comprised of a gas-permeable, biocompatible polymer, such as ethylene vinyl acetate, polyanhydride, polyglycolic acid, collagen, polyorthoester, or polylactic acid. The entire body, or at least an inner surface, of the device is coated or impregnated with the protease inhibitor. The device is disposable and provided in sterile packaging, to be implanted by the patient and worn for a selected treatment period, preferably for the full duration of a period of closed eye tear production (e.g., overnight) for maximum therapeutic efficacy.

Liposomal suspensions may provide useful, pharmaceutically acceptable carriers for formulating antiproteolytic compositions of the invention. These may be prepared according to methods known to those skilled in the art, for example, as described in U.S. Pat. No. 4,522,811 (incorporated herein by reference). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the protease inhibitor is then introduced into the container. The container is swirled by hand to free lipid material from the sides of the container and to disperse lipid aggregates, thereby forming the liposomal suspension.

The pharmaceutical compositions for use within the invention may also contain pharmaceutically acceptable auxiliary substances as required to approximate physiological conditions, such as pH-adjusting and buffering agents, tonicity-adjusting agents and the like, for example, sodium acetate, sodium lactate, sodium chloride, potassium chloride, calcium chloride, etc. The concentration of the antiprotease in these formulations can vary widely, i.e., from less than about 0.05%, usually at least about 0.5%, to as much as 15 or 20% by weight, and will be selected primarily by fluid volumes, viscosities, etc., in accordance with the particular mode of administration selected.

In preferred methods within the invention, mammalian subjects, including human patients, suffering from protease-mediated corneal disorders are treated by administering to the patient a pharmaceutical or therapeutic composition comprising an effective amount of one or more antiproteases, or a pharmaceutically acceptable derivative or complex thereof, in a pharmaceutically acceptable carrier or diluent.

The active antiprotease is included in the pharmaceutically acceptable carrier or diluent in an amount sufficient to deliver to a patient an antiinflammatory effective amount without causing serious adverse side-effects in the patient treated. The active compound is preferably administered to achieve peak concentration of the antiprotease in tear fluid or corneal tissue of the patient within about 1–4 hours after administration. Concentration of the antiprotease in pharmaceutical compositions and devices of the invention will depend on such factors as absorption, distribution, inactivation, degradation, and flushing of the antiprotease, as well as other factors known to those of skill in the art. It is to be noted that dosage values will also vary with the severity of the condition to be alleviated. It is to be further understood that for any particular subject, specific dosage regimens may be adjusted over time according to the professional judgment of the person administering or supervising the administration of the compositions, and that the concentration ranges set forth herein are exemplary only and are not intended to limit the scope or practice of the invention.

In view of the description and examples provided herein, the methods of the invention are shown to be useful for treating a wide variety of inflammatory conditions and diseases. In particular, the methods of the invention can be employed to treat keratoconus and other corneal disease or conditions characterized by aberrantly high proteolytic activity or damage attributable to aberrant proteolytic processes. Other conditions indicative of treatment using the compositions and methods of the invention include, but are not limited to, corneal ulcers, allergic conditions, bacterial infection, viral infection, corneal injury and post-surgical wound healing.

The pharmaceutical formulations administered within the methods of the invention must be opthalmically acceptable. In general, compounds and formulations with a therapeutic index of at least 2, preferably at least 5–10, more preferably greater than 10, are opthalmically acceptable. As used herein, the therapeutic index is defined as the EC50/IC50, wherein EC50 is the concentration of compound that provides 50% inhibition of a target proteolytic activity (e.g., proteolysis by a specific protease, or histopathologic change attributed to proteolysis) compared to a relevant control, and IC50 is the concentration of compound that is toxic to 50% of target cells (e.g., keratocytes in an in vitro toxicity assay). In this context, cellular toxicity can be measured by direct cell counts, trypan blue exclusion, or various metabolic activity studies such as 3 H-thymidine incorporation, as known to those skilled in the art.

The following examples are offered by way of illustration, not by way of limitation.

EXAMPLE I

PROTEASE INHIBITION AND DETERMINATION OF ANTIPROTEOLYTIC ACTIVITY IN TEAR SAMPLES

The present example describes representative protocols for determining inhibition of proteolytic activity in extracorneal fluid (tears) of rabbits and human subjects treated using the compositions and methods of the invention. This example involves ocular administration of one or more protease inhibitors to suitable test and control subjects, followed by immunological and/or enzymatic assays to identify and quantify resultant proteolytic activity and relevant associated parameters. It will be understood that the following protocols, which exemplify suitable assays for determining caseinolytic activity, are adaptable for additional proteolysis assays using various sample types, target proteases, and protease inhibitor types, concentrations, and formulations (e.g., eyedrops, topical gels, microparticulate solutions, etc.). In particular, the methods described herein below are readily adapted to further define preferred compositions and methods of the invention by determining, e.g., (1) optimal timing and duration of protease inhibitor treatments; (2) optimal inhibitor type(s) for inhibiting different target protease(s) (e.g., by selecting different classes or species of preferred inhibitor(s), or by using inhibitor variants such as recombinant or synthetically modified inhibitors); (3) optimal inhibitor concentration(s); and (4) preferred delivery vehicles and methods.

Animal Subjects and Treatments

Useful animal subjects for the various examples presented herein are rabbits (e.g, New Zealand or Dutch-belt pigmented rabbits), which provide a generally faithful model system for evaluating human corneal pathology and treatment. Rabbit subjects are screened to eliminate complicating ocular conditions, such as allergies or infection, and are selected for comparable age, sex, weight, and other potentially relevant factors between sample groups. All experiments involving rabbits conform to the ARBO Resolution of the Use of Animals in Research.

In the case of in vitro and in vivo antiproteolytic assays involving non-invasive collection methods, e.g., collection of tear samples and postoperative or postmortem collection of tissue samples, human subjects are also useful as described further herein below. As in the case of rabbit subjects, human subjects are also normalized to eliminate significant differences in medical histories, clinical features, or histopathologic characteristics, such as degree of scarring or keratometric readings.

Various groups of test and control subjects, and various treatments of said subjects, are used to exemplify and further characterize the compositions and treatment methods of the invention. These various subjects and treatments are chosen to fit particular experimental designs to yield desired data, as will be understood by those skilled in the art in accordance with the teachings herein. Preferred test subjects in many instances are non-human mammalian and human subjects that exhibit a specific corneal disease or disorder amenable to treatment by the compositions and methods of the invention. Thus, for example, human subjects exhibiting symptoms of keratoconus (preferably separated into mild, intermediate, and severe pathological classes according to clinical indicia such as keratometric values), keratoconus-like corneal defects, corneal ulcers, bacterial infection, and other corneal diseases or conditions associated with aberrant proteolytic activity are recruited as test subjects. These and other test subjects are typically treated alongside suitable control subjects, for example control subjects that present similar pathologies as test subjects but are differentially treated (e.g., using a placebo administration, altered dose, alternative timing or mode of administration, etc.), or control subjects that have healthy corneas and are treated similarly to diseased test subjects.

Assays described in the following examples are conducted using samples taken from test and control subjects, typically before, during, and after treatment with a protease inhibitor formulation. In general, these assays will incorporate standard proteolytic activity assays along with control assays that determine relevant associated parameters, for example, levels of target proteases and their substrate proteins, quantitative measurements of proteolytic activity (e.g., based on detection of substrate protein levels, inhibitor cleavage products, protease/inhibitor complexes, or based on enzymatic assay readings), and levels of endogenous and exogenous protease inhibitors.

The mode, timing, and duration of treatment is also varied as described in further detail below. Most commonly, antiproteolytic formulations of the invention are administered topically, e.g., in the form of drops, gels, creams, microparticulate solutions, and the like. Alternatively, antiproteolytic formulations are delivered directly to a corneal tissue or other site (e.g., vitreous humor) using, e.g., permeabilizing formulations or suitable injection methods.

For determining short-term delivery kinetics and efficacy, antiproteolytic formulations are administered to subjects in a one-time dose, and proteolytic activity and associated parameters are determined for samples taken at selected periodic time increments (e.g., at 1 hr, 4 hr, 8 hr, 16 hr, and 24 hr post-administration). For determining longer-term delivery kinetics and efficacy, antiproteolytic formulations are administered to subjects in a single, sustained-delivery dose, or in multiple doses (e.g., daily), and measurements of proteolytic activity and associated parameters are carried out over periods of days, months, or years.

Concentration of protease inhibitors and other agents incorporated within the formulations of the invention will vary in accordance with such factors as the delivery vehicle or carrier employed, the timing and duration of the selected treatment regimen, the identity, stability and activity of the inhibitor, and other factors, as will be apparent to the artisan practicing the invention. Exemplary formulations for α2-M will comprise the inhibitor at a concentration of between approximately 0.2 μg/ml and 1.0 mg/ml. Preferably, the inhibitor is present in a concentration of about 0.1–1.0 μg/ml, more preferably at a concentration of about 0.5 μg/ml. Exemplary formulations for α1-antitrypsin will comprise the inhibitor at approximately the same range of concentrations, with the most preferred concentration being between about 1.0 and 5.0 μg/ml.

Collection and Processing of Tear Samples

The conditions under which tear samples are collected, prepared and stored must be carefully controlled because the mode, rate and method of sample collection can alter the composition of the fluid being analyzed. For the purpose of the present example, tears are obtained according to the guidelines of the Association for vision Research and Ophthalmology (ARVO) and the Geneva Conven-tions, from a representative pool of subjects previously trained and experienced to self-collect tear samples using microcapillary tubes. All subjects are free of apparent external ocular disease and atopic ocular reaction.

Two types of tear samples, reflex tears (R tears) and closed eye tears (C tears) (described in further detail herein below), are collected. R tears are collected using 25-μl cali-brated disposable microcapillary tubes (Aqua-Cap™, Drummond Scientific Co., Broomall, Pa.). Two- to four-microliter-sized samples representative of the fluid present under the lid after overnight eye closure are collected immediately upon awakening in calibrated 1–5 μl microcapillary tubes (Drummond Scientific Co.). All samples are transferred to siliconized Eppendorf tubes and transported on ice to the laboratory within two to three hours. To facilitate handling, C tear samples are diluted 1:1 with phosphate buffered saline (PBS) and centrifuged twice in an Eppendorf centrifuge for 30 min each at 11,000 rpm at 4° C. Some R samples are concentrated at 4° C. using a 1 kD cutoff centrifugal ultrafilter (filtron, Northborough, Masas.). The resulting supernatants are stored at −78° C. in small volumes and discarded after a single use.

R and C Tear Supernatant Analysis

R tear concentrates and pooled C samples are chromatographed using a size exclusion analytical column (TSK G 4000 SW (7.5×300 mm)) in 0.1 M PBS pH 5.0 containing 0.5 M NaCl, at a flow rate of 0.25 ml per min with detection at 254 nm (45). The eluent is collected in multiple fractions, although some of the major UV-absorbing (protein) peaks may be subdivided into high and low molecular weight ends. Samples are concentrated on ultrafilters (pre-conditioned with HPLC buffer) for further analysis. To confirm the relative size range of the eluted material, the column is calibrated, using protease and antiprotease standards and a commercial mixture of gel filtration chromatography standards (Bio-Rad).

Zymographic and Reverse Zymographic Analysis

Zymography is carried out using methodologies as described elsewhere (Fernandez-Resa et al., *Anal. Biochem.* 224:434–435, 1995; and Heussen et al., *Anal. Biochem.* 102:196–202, 1980, each incorporated herein by reference) and modified according to Sakata et al. (*Curr. Eye. Res.* 16:810–819, 1997, incorporated herein by reference). The methods set forth below are described for caseinolytic assays detecting and/or quantifying selected proteases (elastase, cathepsin G and proteinase-3), protease inhibitors (alp1, α1-Achy, SLP1, elafin, and α2-M), and protease/inhibitor complexes. However, these methods are also routinely adaptable for detecting and measuring other useful proteases and protease inhibitors within the invention, e.g., by substituting the specific immunological probes, enzymatic reagents, etc.

Briefly, samples are separated at 4° C. without heat denaturation on pre-electro-phoresed 12% SDS-PAGE minigels containing 1 mg/ml of a test proteolytic substrate (e.g., casein-Sigma #7891) run under non-reducing (nr) conditions at 25 mA per gel, until the lowest molecular weight marker (See Blue™ markers, Novex, San Diego, Calif.) reaches the bottom of the gel. Protease standards, for example human glu-plasmin (American Diagnostics Inc., Greenwich, Conn.), cathepsin G, elastase (Calbiochem, La Jolla, Calif.) and proteinase-3 (Elastin product Company, Inc., Owensville, Mo.) are selected for each proteolytic assay. Proteins are renatured for 60 min in 2.5% (v/v) Triton X-100, then incubated for 18–20 h at 37° C. in developing buffer (0.05 M Tris-HCl pH 7.5, 5 mM CaCl2, 0.2 M NaCl and 0.02% (v/v) Brij 35) and stained with 0.5% coomassie Brilliant Blue.

Proteolytic activity is visualized as clear zones against a blue background. To estimate the concentration of free elastase-like activity in the instant, exemplary assay, two or three dilutions of a sample are co-electrophoresed with a series of dilutions of freshly prepared elastase (5–30 ng) with the area of the three lytic bands either visually estimated or video-digitized and computer integrated.

Samples may be screened for low molecular weight elastase inhibitors by reverse zymography, using 18% SDS-PAGE-casein gels run, equilibrated and developed as above but with 400 ng of human elastase added to 10 ml of developing buffer. Free inhibitor activity appears as blue bands against a semi-clear background. Also discernable are endogenous proenzymes activated by elastase which appear as bands with excessive lytic activity when compared to a duplicate zymogram developed without elastase. As a further control, an 18% SDS-PAGE gel is run without added casein.

Sodium Dodecyl Sulfate-Polyacrylamide Gel Electrophoresis (SDS-PAGE) and Western blot Analysis The presence in tear fluid of blocking factors and non-specifically reacting substances complicate immunological identification and quantification of tear proteins, especially in C tear fluid. Thus, the Western blot assays used and adapted herein (Sakata et al. (*Curr. Eye. Res.* 16:810–819, 1997; Kowal, *Arthritis and Rheumatism* 37:1206–1211, 1994; Velleman, *BioTechniques* 18:1056–1058, 1995; and Venembre et al., *Clinica. Chimnica. Acta.* 227:175–184, 1994, each incorporated herein by reference) are selected to overcome these problems so as to provide useful quantitative data, as demonstrated in the above cited reports for the protease inhibitors α2-M, alp1 (58 kDa), α1-Achy (68 kDa), SLPI (11.7 kDa), elafin (6–9 kDa), cystatin C (13.5 kDa), and associated complexes and breakdown products.

For each assay, the conditions of electrophoresis (such as mode of sample preparation, types and percentage of gels) are optimized to obtain maximal antigenic sensitivity and to resolve the antigens in question from overlapping blocking tear proteins as well as from non-specific reacting substances. High and mid-molecular weight range antigens are separated by fine tuning the conditions of separation on pre-cast 4–20% gradient minigels. Low molecular weight entities are similarly separated on either 16 or 18% minigels, or 10–20% Tricine gradient minigels (Novex). Samples are run either under reducing or non-reducing (r, nr) conditions at ambient temperature using a modified method of Laemmli (*Nature* 227:680–685, 1970) as instructed by the gel manufacturer. Molecular weight markers include prestained kaleidoscope standards (Bio-Rad #161–0324) and See Blue™ markers (Novex) which range in size from 6 to 250 kDa. In all instances, negative controls consist of identical blots probed with the appropriate dilutions of non-immune goat, sheep or rabbit serum or purified IgG and mouse IgG1 (Jackson Immunochemicals, West Grove, Pa. and Sigma, St. Louis, Mo.), which are run, processed and analyzed simultaneously. Exemplary positive controls for protease inhibitors include elafin (Peptides International, Louisville, Ky.), SLPI (R and D System Inc., Minneapolis, Minn.), α1-Achy, alp1, α2-M and cystatin C (Calbiochem) and freshly generated complexes of elastase with alpI and SLPI prepared as detailed by others (Rao et al., *Am. J. Resp. Cell Mol. Biol.* 8:612–616, 1993; and Stockley et al., *Clin. Sci.* 66:217–224, 1984, each incorporated herein by reference).

For quantitative determinations, multiple dilutions of a given tear sample along with a series of dilutions of the appropriate protein standard are run in tandem on a gel. The gels are then equilibrated in 20% v/v methanol, 25 mM Tris-Base, 192 mM Glycine buffer pH 8.3 and transferred (Bio-Rad miniblot apparatus) overnight at 30V at 4° C. Antigens larger than 14 kD are transferred onto Immobilon-P membranes, those smaller than 14 kDa are transferred onto Immobilon-PSq (pore size $0.1\mu$) or $0.1\mu$ nitrocellulose.

Immunodetection is carried out at ambient temperature with the membranes incubated for 1 h in blocking buffer (100 mM Tris-HClm pH 7.4, 150 mM NACl, 0.1% Tween 20, 0.2% I block (Tropix, Bedford, Mass.)). This is followed by incubation for 1 h in 1:100–1:2,000 v/v dilution of primary antibody in blocking buffer. To maximize detection of reactive products and complexes, anti-bodies with known narrow target antigens are avoided. In this context, exemplary primary antibodies for detecting proteases and protease inhibitors are sheep polyclonal antibodies to elastase, α2 M and alp1 (Binding Site), rabbit polyclonal antibodies to cystatin C (DAKO, Glostrup, DK), proteinase-3 (Elastin product company), elafin (Peptides International) and cathepsin G (Calbiochem), goat polyclonal antibodies to SLPI (R and D systems, Inc.) and monoclonal antibodies to α1-Achy (Calbiochem).

After primary antibody incubation and washing, the membranes are incubated for 1 h in a 1:30,000 v/v dilution of an appropriate alkaline-phosphatase conjugated secondary antibody affinity purified against human serum proteins (Sigma), in blocking buffer. The membranes are then washed and reacted with NBT-BCIP substrate (Pierce, Chicago, Ill.).

Blots are scanned using a flat bed scanner and quantitatively integrated, based upon the peak area (area multiplied by the intensity) of each band, using Sigma Image Analysis™ software (Jandel Scientific, San Gabrial, Calif.). Standard curves are generated for each blot and the amount of a given protein in a sample is determined by extrapolation.

To estimate concentrations of inhibitor-protease complexes and degradative products, all detected species are assumed to exhibit antigenicity similar to the native antiprotease. Although it is recognized that this will not always hold true, loss of detected epitopes between free and complexed species will be readily discerned and accommodated by use of alternative immune reagents.

Conventional Western blot procedures are too insensitive to allow detection of nanogram quantities of polymorphonuclear leucocyte (PMN) cell proteases. Accordingly, an alternate blotting protocol is employed involving pre-incubation of the samples with detergent and a protease inhibitor, electrophoresis at 4° C. (to reduce adherence and proteolysis), and blot transfer under basic conditions (to enhance the efficiency of transfer of basic proteins). Szewczyk et al., *Anal. Biochem.* 150:403–407, 1985, incorporated herein by reference.

Immunoprecipitation Reactions

C tears and the HPLC fractions are immunoprecipitated with antibodies to a selected protein, glycoprotein, protease or antiprotease by incubation at 4° C. overnight. The complexed and free IgG is then adsorbed onto recombinant protein G immobilized beads (UltraLink™, Pierce) for a h at room temperature. The residual protein in the supernatant is acetone precipitated at −20° C. while the bound material is subjected to multiple washings and then eluted from the beads in SDS-Page loading buffer (nr) at 50° C. for 10 min. Samples are then subjected to zymographic analysis. Alternatively, for Western blot analysis samples are eluted from the beads by boiling in 2×SDS-PAGE buffer (under r or nr conditions) and centrifuged. Controls are immunoprecipitated with non-immune serum.

By applying the foregoing procedures and principles, it will be shown that the antiproteolytic compositions and methods of the invention effectively inhibit proteolytic activity in extracorneal fluid (tears). By selecting a multi-specific protease inhibitor (i.e., an inhibitor which targets multiple protease species) such as α2-M and alp1, or by combining multiple protease inhibitors in a single treatment formulation, effective inhibition can be achieved against multiple proteases involved in a corneal disease process. Accordingly, the methods of the invention will be shown to inhibit corneal disease mediated by exposure of the cornea to aberrantly elevated protease activities in tears.

Adaptation of the foregoing procedures as disclosed herein will further demonstrate that antiproteolytic effects against a broad range of proteases (e.g., acid esterases, acid phosphatases, acid lipases, cathepsins, collagenases, elastases, tryptases, chymases, kinins, kalikreins, tumor necrosis factors, chymotrypsins, stromelysins, and matrix metalloproteases) that alleviate or prevent corneal disease can be achieved by ocular administration of protease inhibitors selected from a broad range of inhibitors, including aspartic, serine, cysteine, or metallo-protease inhibitors. These may be obtained from natural or artificial sources, and can include modified inhibitors that vary in structure from native inhibitors while retaining substantial antiprotease activity. Species of protease inhibitors useful within this context include alp1, α2-M, SLP1, β1-antigellagenase, α2-antiplasmin, serine amylyoid A protein, α1-Achy, cystatin C, inter-α-trypsin inhibitor, elafin, elastinal, aprotinin, phenylmethyl sulfonyl fluoride, E-64, leupeptin, and the metalloprotease inhibitors TIMP-1, TIMP-2, and 1, 10-phenanthroline.

Quantitative analyses based on the foregoing procedures will further demonstrate that administration of the antiproteolytic compositions of the invention yields at least about a 20% reduction of proteolytic activity compared to a relevant baseline or control value at an ocular target site. Moreover, when these compositions are administered in preferred formulations and treatment protocols in accordance with the examples below, proteolytic inhibition of approximately 50–80% compared to baseline/control values can be achieved, while in some instances administration of these compositions will yield effective neutralization of proteolytic activity corresponding to a reduction of about 85–100% of baseline/control proteolytic activity.

EXAMPLE II

ENHANCED PROTEASE INHIBITION IN CLOSED-EYE TEARS AND ASSOCIATED INHIBITION OF PROTEOLYSIS AND ASSOCIATED HISTOPATHOLOGIC CHANGES IN KERATOCONIC CORNEAS

The present example describes representative protocols for inhibiting proteolytic activity during periods of closed eye tear production and for demonstrating that this treatment results in enhanced inhibition of proteolysis in the extracorneal fluid and cornea and associated histopathological changes in the cornea of patients suffering from keratoconus. As in the preceding example, this protocol involves ocular administration of one or more protease inhibitors to suitable test and control subjects, followed by immunological and/or enzymatic assays to identify and quantify resultant proteolytic activity and associated parameters.

However, the present example is specifically directed to administration of an antiprotease composition to patients during periods of closed eye tear (C tear) production. In addition, the protocol of the instant example incorporates correlative immunological assays, enzymatic assays, and/or histopathological analyses of corneal tissues, in addition to the above described assays using tear samples. These additional assays allow confirmation that protease inhibition in closed eye tears results in associated inhibition of proteolytic processes in corneal tissues (e.g., as demonstrated by reduction in the activity of specific target protease(s), or by long-term inhibition of histopathological changes such as fragmentation of Bowman's layer).

Administration of the antiprotease compositions of the invention during periods or closed eye tear production greatly enhances the efficacy of corneal therapy according to the methods of the invention. This is due in part to the prolonged retention of the antiprotease composition attributable to a reduction in tear flushing between closed eye and reflex tear periods. This enhanced efficacy is also attributable to fundamental differences in the processes and regulation of proteolysis that characterize the closed eye, versus reflex tear environments.

In the open eye state, the aqueous tear layer is derived primarily from an inducible, neurologically controlled, lacrimal secretion, which is in constant dynamic equilibrium. In terms of host-defense mechanisms, this fluid is believed to function in conjunction with the blink as a critical component in a passive barrier system, removing potential pathogens as well as immune and inflammatory mediators from the ocular surfaces. Concordant with this capability, the open eye fluid is of limited nutritional value and is enriched in anti-microbial and antiinflammatory constituents (van Haeringen, *Surv. Ophthalmol.* 26:84–96, 1981; Kijlstra, *Reg. Immunol.* 3:193–197, 1991, each incorporated herein by reference).

It has been shown that the anti-inflammatory armament of reflex tears includes trace amounts of several serpins: alp1, α1-Achy and α2-M, whereas the principal serpin in R tears is SLPI, an 11.7 kDa (unglycosylated form) elastase and cathepsin Gspecific inhibitor (Sathe et al., *Current Eye Res.* 348–362, 1998, incorporated herein by reference). Based upon the calculated molar ratios of the observed serpins and the unique presence of two rather than one serine protease binding sites on SLPI, Sathe and coworkers report that SLPI accounts for 95% or more of the total elastase inhibitory activity in R-type tear fluid.

This finding does not exclude an important ancillary role in R tears for other serpins. Although SLPI is a potent inhibitor of elastase and cathepsin G (Nadziejko et al., *Am. J. Resp. Crit. Care Med.* 152:1592–1598, 1995; Rao et al., *Am. J. Resp. Cell Mol. Biol.* 8:612–616, 1993; and Thompson et al., *Proc. Natl. Acad. Sci. USA* 83:6692–6696, 1986, each incorporated herein by reference), it has no capacity to inhibit proteinase-3, a major PMN product. In contrast, alp1 and elafin are potent inhibitors of proteinase-3 (Bergenfeldt et al., *Scandinavian Journal of Clinical & Laboratory Investigation* 52:823–829, 1992; and Wiedow et al., *Biochem. Bioph. Res. Co.* 174:6–10, 1991, each incorporated herein by reference). Bergenfeldt et al. provide data that suggests that SLPI and alp1 function in a synergistic manner in other mucosal tissue to neutralize the entire spectrum of PMN cell serine proteases (Bergenfeldt et al., *Scandinavian Journal of Clinical & Laboratory Investigation* 52:823–829, 1992, incorporated herein by reference).

SLPI has antimicrobial properties that are consistent with a barrier defense function. SLPI is cytotoxic to *E. coli* and *Staphylococcus aureus* (Hiemstra et al., *Infection & Immunity* 64:4520–4524, 1996; and Miller et al., *J. Bacteriol.* 171:2166–2172, 1989, each incorporated herein by reference) and inhibits the transmission and replication of HIV virus in cell culture (McNeely et al., *J. Clin. Invest.* 96:456–464, 1995, incorporated herein by reference). Moreover, in respiratory secretions, its highly basic nature has been shown to allow SLPI to selectively complex with acidic sialoglycoproteins and other acidic polymers (Van-Seuningen et al., *Int. J. Biochem.* 24:303–311, 1992; Van-Seuningen et al., *Biochem. J.* 281:761–766, 1992; and Nadziejko et al., *Am. J. Respir. Cell & Mol. Biol.* 11:103–107, 1994, each incorporated herein by reference). In the respiratory tract, SLPI presumably is localized as an integral part of the protective barrier overlying the epithelium. Whether a similar functional relationship exists in the eye between SLPI, ocular mucin, and tear sialoglycoprotein derived from the epithelial plasma membrane is presently unknown (Sack et al., *Curr. Eye Res.* 16:577–588, 1997, incorporated herein by reference).

While the serine protease neutralizing capacity of R fluid is limited, in the open eye during inflammation or infection this capacity can be readily augmented through: (1) an increased rate of fluid turnover, (2) an increased inclusion through vascular leakage of mid-molecular weight range serum antiproteases (e.g. alp1) and (3) a possible up-regulation of locally synthesized antiproteases. Upon eye closure the situation changes dramatically.

During closed eye tear production, the rate of inducible lacrimal secretion decreases at least tenfold (Sack et al., *Curr. Eye Res.* 15:1092–1100, 1996, incorporated herein by reference), with ongoing flow continuing in the form of a much slower constitutive-type of secretion composed almost exclusively of sIgA (Sack et al., *Invest. Ophthalmol. Vis. Sci.* 33:626–640, 1992, incorporated herein by reference). This greatly restricts the capacity of the external ocular environment to neutralize protease activity by passive dilution. Moreover, overnight eye closure is associated with the induction of a subclinical state of inflammation, as evidenced by an increased level and conversion of complement (Sack et al., *Invest. Ophthalmol. Vis. Sci.* 33:626–640, 1992; Tan et al., *Curr. Eye Res.* 12:1001–1007, 1993; Sakata et al., *Curr. Eye Res.* 16:810–819, 1997, each incorporated herein by reference) and the recruitment, activation and degranulation of large numbers of PMNs (Sack et al., *Invest. Ophthalmol. Vis. Sci.* 33:626–640, 1992; Tan et al., *Curr. Eye Res.* 12:1001–1007, 1993; Thakur et al., *Invest. Ophthalmol. Vis. Sci.* 37 Suppl.: S234, 1996; Sakata et al., *Curr. Eye Res.* 16:810–819, 1997, each incorporated herein by reference). This results in a stagnant layer enriched in serine proteases and complement products.

The enrichment of serine proteases in closed eye tears raises the question as to how autolytic cell damage is prevented during this period. In further studies, it has been reported that PMN cell-induced proteolytic damage is avoided at least in part by a build up of four rapid-reacting serpins, with SLPI, alpi and $\alpha$1-Achy reportedly acting as the principal functional entities. These serpins have a combined spectrum of activity such that all known PMN serine proteases can be inactivated. Sathe et al., *Current Eye Res.* 348–362, 1998, incorporated herein by reference. These investigators have also reported that under normal conditions C tear fluid invariably contains a large reserve of these rapid-reacting inhibitors, as well as a secondary reserve of $\alpha$2-M. However, the majority of $\alpha$2-M in C tear fluid from most donors remains intact. Notably, although $\alpha$2-M reacts with PMN cell proteases, it does so at only a relatively slow rate (Swenson et al., *J. Biol. Chem.* 254:4452–4456, 1979, incorporated herein by reference). This suggests that, in most individuals throughout the period of eye closure, there is a sufficient pool of rapid reacting serpins available so as to quench the released proteases in sufficient time to prevent reaction with $\alpha$2-M (Sathe et al., *Current Eye Res.* 348–362, 1998, incorporated herein by reference).

Additional research relating to the unique attributes of closed eye tears has focused on the role of secretory IgA in preventing pathogenic impacts within the relatively stagnant closed eye environment. In this context, Sack et al. (*Invest. Ophthal. & Vis. Sci.* 33:626–640, 1992, incorporated herein by reference) report that secretory IgA undergoes nearly a 40-fold increase in concentration during the transition from reflex to closed eye tear production, thus becoming the principal closed eye tear constituent. In some cases, closed eye tears that are least contaminated with fresh reflex fluid exhibit secretory IgA at levels exceeding 75% of the total tear protein. This dramatic shift in tear composition that occurs upon eye closure, coupled with subclinical inflammation, is suggested to play a vital role in protecting ocular surfaces in the hostile, closed eye environment. In particular, upon eye closure, lid movement and tear flow are greatly reduced, restricting the efficiency with which microorganisms can be cleared from external ocular surfaces and precluding oxygen and carbon dioxide exchange at the tear:air interface. A secretory IgA-enriched fluid presumably augments the effectiveness of the external barrier to microbial adherence and increases the efficiency by which pathogens can be processed by the immune and inflammatory systems. An active inflammatory reaction, in turn, allows a rapid response to any breach in this barrier, while enhancing the efficiency of gas exchange between peripheral blood vessels and tears through vasodilation.

Although the closed eye environment is thus uniquely equipped with protective mechanisms against pathogenic infection, including a battery of fast-acting protease inhibitors, it is nonetheless found that the compositions and methods of the invention are particularly useful in preventing proteolytic damage and attendant corneal pathogenesis when administered during closed eye periods.

Animal Subjects and Treatments i) Comparison of Treatments During Periods of Closed Eye and Reflex Tear Production.

For determining and quantifying the effects of antiproteolytic compositions administered during periods of closed tear production, both animal and human subjects may be used in accordance with the preceding example. The same assays as detailed above are employed, with the modification that test and control samples are represented by subjects to whom an antiproteolytic composition is administered, at similar doses and for comparable duration, entirely during a reflex tear or closed eye tear production period, respectively. Values obtained from these assays are compared against one another after normalization to baseline values (e.g., values determined in baseline control samples to which a placebo is administered) and determination of the associated parameters outlined above. These results thus enable confirmation that the compositions and methods of the invention yield a substantially greater antiproteolytic effect during periods of closed eye tear production compared to periods of reflex tear production.

ii) Antiproteolytic Activity in Corneal Tissues by Antiprotease Treatment During Periods of Closed Eye and Reflex Tear Production.

In addition to the foregoing analyses, alternate test and control samples are utilized to document that closed eye administration of antiproteolytic compositions of the invention results in quantitative inhibition of proteolysis, not only in the extracorneal fluid, but also in the corneal tissue of treated subjects. For this purpose, the antiproteolytic compositions are administered, as above, to rabbit subjects during closed eye and reflex tear production periods. A protracted treatment regimen is employed, wherein the antiproteolytic composition is administered daily for one week. The subjects are then sacrificed and corneal tissues are isolated and processed for analysis of proteolytic activity. These analyses are conducted according to the methods described above or, alternatively, using an enzymatic assay exemplified as follows.

Protease Extraction From Corneal Tissues

Prior to extraction, corneal tissues are stored in liquid nitrogen. Tissues are then pulverized in liquid nitrogen using a small ceramic mortar and pestle, and homogenized in 0.01 M potassium phosphate buffer, pH 7.4, containing 0.2 M sodium chloride. Homogenates are transferred to Eppendorf tubes and centrifuged for 10 minutes to pellet insoluble material. The supernatants are then removed and, after the addition of glycerol (10% v/v, fmal concentration), are stored for assaying at −20° C.

Enzymatic Assays

Proteases present in soluble protein preparations from corneal tissues of treated and control subjects are analyzed and quantified by assaying against nitrophenyl acetate as a substrate and by substrate (e.g., gelatin) eletrophoresis. Smith et al., Eye 9:429–433, 1995, incorporated herein by reference. All proteases possess acyl transferase activity and will catalyze the liberation of 4-nitrophenol from 4-nitrophenyl acetate. Thus, acyl transferase assays are useful within a variety of protocols herein. In the present example, substrate stocks (0.5 mM) are prepared in dimethyl sulphoxide (DMSO). The enzyme preparations are assayed against this substrate (0.025 mM) in 0.01 M potassium phosphate buffer, pH 7.2 containing 0.2 M sodium chloride in a total volume of 1 ml. The kinetics of nitrophenol production (calculated E340=7620) is followed spectrophotometrically at 37° C.

Substrate Gel Electrophoresis

The gelatinases isolated from subject corneal tissues are separated and visualized after electrophoresis on polyacrylamide gels (8.5%) containing gelatin (1 mg/ml), as described by Unemori and Werb (*J. Cell Biol.* 103:1021–31, 1986, incorporated herein by reference). The sample solutions contain the ionic detergent sodium dodecyl sulfate (SDS, 1% w/v) and glycerol (10% v/v), and are applied to the gels without boiling or reduction. After electrophoresis, the gels are incubated in Triton X100 (2.5% v/v) for 30 minutes at 37° C., rinsed in distilled water and then incubated for approximately 16 hours in 50 mM Tris HCl, pH 7.4, containing 5 mM calcium chloride and 0.02% (w/v) sodium azide. After rinsing with distilled water, they are then stained with Coomassie Blue [2.5% w/v in an aqueous solution of methanol (45%) and glacial acetic acid (10%)], and destained with aqueous methanol/acetic acid (5% and 7.5% v/v, respectively).

Protein Estimation

Protein concentration is estimated spectrophotometrically from the relationship OD2259.18=1.0 mg/ml. Hall et al., Genetics 81:427–35, 1975, incorporated herein by reference.

Results from the foregoing assays enable confirmation that the compositions and methods of the invention yield an antiproteolytic effect in both extracorneal fluids and corneal tissues, which effect is significantly enhanced during periods of closed eye tear production compared to periods of reflex tear production.

iii) Prevention of Pathogenic Structural Changes in Keratoconic Corneal Tissues by Antiprotease Treatment During Periods of Closed Eye and Reflex Tear Production.

Additional assays are also utilized herein to document that administration of antiproteolytic compositions of the invention results in quantitative inhibition of structural degradative changes in the corneas of patients suffering from keratoconus. For this purpose, human subjects are enlisted presenting with advanced stage keratoconus and prospectively scheduled for keratotomy or other surgical procedure during which corneal tissues will be incidentally available for harvest. Prior to the scheduled surgical procedure, antiproteolytic compositions of the invention and placebo formulations are administered to test and normal control groups of patients during closed eye and reflex tear production periods. This treatment protocol involves an even more protracted regimen in order to manifest inhibition or reversal of corneal structural changes, wherein the antiproteolytic composition is administered daily for two to six months prior to surgery. At the time of surgery, corneal tissues are harvested and a portion of each harvested sample is processed for analysis of proteolytic activity. These analyses are conducted according to the methods described above or, alternatively, using a different enzymatic assay which further compares trypsin-activated versus non-activated samples, as described by Rehany et al. (*Ann. Ophthalmol.*:751–754, 1982, incorporated herein by reference) and summarized below. Remaining corneal tissues are processed for correlative histopathological examination, as described below.

Preparation of Substrate

An alternative enzymatic assay for determining proteolytic activity within the invention employs acid-soluble, native 14 C-proline (specific activity >225 mCi/mmole) and 14 C glycine (specific activity >90 mCi/mmole) as radioactive markers. Cold 0.5 N acetic acid is used to extract labeled collagen from the skin of young guinea pigs, which is further purified using a trichloracetic acid-ethanol mixture. Gross, J. Exp. Med. 107:247–263,1958, incorporated herein by reference. The collagen solution is lyophilized and stored in vacuum at −20° C. Before its use, a 0.2% solution of collagen in 0.4 M of sodium chloride −0.005 M tris of (hydroxymethyl) aminomethane, pH 7.6, is prepared under sterile conditions. Aliquots of 0.5 mL containing about 25,000 counts per minute (cpm) are placed in 3-mL centrifuge tubes which are then heated to 37° C. Thermally reconstituted collagen fibers, which serve as substrate for collagenase assay, are thus obtained.

Preparation of Enzyme

Corneal tissue samples from closed eye and reflex eye subgroups of antiprotease treated and non-treated subjects are each divided into three enzyme assay sample groups, a normal control group, a trypsin activated test group, and a nonactivated test group. Corneal buttons from each sample are incubated at 37° C. in an organ culture system containing Medium 199 supplemented with penicillin (250 IU/mL), streptomycin (10 µg/mL), and ascorbic acid (50 µg/mL). Each sample is placed in 10 mL of medium and flushed with O2 for two minutes. Media are changed daily for three days and then pooled. Pooled media are dialyzed against distilled water, lyophilized, and dissolved in 2.5 mL of sodium chloride-tris(hydroxymethyl) amino-methane buffer supplemented with 0.005 M of calcium chloride. One milliliter of each sample is incubated with 5 µg of trypsin at 25° C. for ten minutes, followed by inactivation of the enzyme with 40 µg/mL of soybean trypsin inhibitor. (Vaes, *FEBS Lett.* 28:198–200, 1972, incorporated herein by reference) Two collagenase preparations were thus obtained: trypsin-activated and nonactivated collagenase.

Collagenase Assay

Aliquots from the concentrated media containing 1,000 µg of protein each (as determined before the incubation with trypsin by the Lowry method (Lowry, *J. Biol. Chem.* 193:265–275, 1951, incorporated herein by reference) are applied in duplicate on top of the collagen gel and incubated at 37° C. for 24 hours. Since equal amounts of protein are used, the number and weight of corneal buttons in each sample does not skew the results of the enzymatic assay. Exemplary controls for this assay include the following: (1) substrate with buffer only; (2) substrate with bacterial collagenase (10 µg); (3) substrate with trypsin (10 µg); and (4) substrate with collagenase and ethylenediamine tetraacetic acid (EDTA) (10 mM).

At the end of incubation, the tubes are centrifuged at 50,000 g for ten minutes to separate solubilized collagen fibers from nondigested fibers. The enzyme activity is assessed by calculating the net percentage of radioactivity in the supernatant fluid relative to the total radioactivity in each assay system. The total radioactivity (total CPM) is estimated by adding the total CPM in supernatant fluid to that left in the undegraded substrate pellet. (Radioactivity is counted in sample aliquots of 50 λ taken from the supernatant fluid and the undegraded substrate after hydrolyzing it with 6.0N hydrochloride). The net percentage of CPM is derived, since there is some radioactivity in the supernatant fluid before adding the enzyme, and is calculated as follows: net % percentage of CPM=CPM in supernatant fluid of sample/total CPM of sample X 100-CPM in supernatant fluid of substrate only.

Histopathological Analysis

Intact corneal tissues (i.e., including epithelial, stromal and Bowman's layers) are processed for histopathological examination to correlate with data from the above enzymatic assays as described by Sawaguchi et al. (*Invest. Ophthal. Vis. Sci.* 35:4010–4014, 1994, incorporated herein by reference). Briefly, treated and control corneal tissues obtained at the time of corneal transplantation are handled and prepared for immunohistochemical staining and correlative dot blot and Western assays according to conventional methods.

For immunoperoxidase staining, the tissues are fixed in 10% formalin, processed, and embedded in paraffin. Five-micrometer-thick sections are cut, deparaffinized, rehydrated and subjected to primary and secondary antibody incubations. To detect levels of exemplary protease inhibitors, the rehydrated sections are incubated first in 10% normal goat blocking serum for 20 minutes and then with polyclonal rabbit antihuman α2-macroglobulin antibodies (1:100 dilution; Dako, Santa Barbara, Calif.) for 1.5 hours. This affinity-purified antibody preparation is monospecific by immunoelectrophoresis against plasma. Alternatively or additionally, primary antibodies to α1-antichymotrypsin and/or α2-antiplasmin (Athens Research Technology, Athens, Ga.) are employed. After incubation with the primary antibody and rinsing with phosphate-buffered saline, the sections are fuirther incubated with biotinylated goat antirabbit IgG (1:500; Vector Laboratories, Burlinghame, Calif.) for 30 minutes, and soaked in 0.3% $H_2O_2$-methanol for 20 minutes to block the endogenous peroxidase. They are subsequently incubated with avidin-biotin-horseradish-peroxidase complex (ABC; Vector) for 30 minutes, and the color reaction is developed with 3,3-diaminobenzidine tetrahydrochloride (Sigma Chemical, St. Louis, Mo.). The sections are dehydrated, mounted in Permont (Fisher Scientific, Itasca, Ill.), and photographed. The brown color shown in the reaction products is examined under light microscopy. For negative controls, normal rabbit IgG is used in place of the primary antibody.

Additional correlative immunohistochemical assays are conducted to determine levels of proteases in the corneal samples. For example, sections are incubated first in 10% healthy goat or healthy rabbit blocking serum for 30 minutes and then incubated with polyclonal sheep anti-human cathepsin B (ICN, Costs, Mesa, Calif.), monoclonal anti-cathepsin G (Pel Freeze Biologicals, Rogers, Ak.), monoclonal antibodies to MMP-1, MMP-2, MMP-3, MMP-9, TIMP-1, TIMP-2, and plasminogen activator inhibitor-1 (Oncogene Science, Cambridge, Ma.), and/or polyclonal antibodies to TPA and urokinase (American Diagnostica, Greenwich, Conn.) for 1.5 hours. The dilutions of antibodies range from 1:10 to 1:200. All antibodies are affinity purified and monospecific, as judged by immunoelectrophoresis. Corneal sections serving as negative controls receive the same dilutions of nonimmune sheep immunoglobulin G (IgG), rabbit IgG, mouse IgG, or anti-digoxigenin. After the primary antibody incubation, the tissue sections are allowed to react with biotinylated goat anti-rabbit (1:250), rabbit anti-sheep (1:250), or goat antimouse IgG (1:500) for 30 minutes. They subsequently are soaked in 0.3% H2O2-methanol for 20 minutes to block the endogenous peroxidase and are incubated with avidin-biotin horseradish peroxidase complex (Vector, Burlingame, Calif.) for 30 minutes. The color reaction is developed with 3,3-diaminobenzidine tetrahydrochloride (sigma Chemical, St. Louis, Mo.). The sections are then dehydrated and mounted in a histologic mounting medium (permount; Fisher Scientific, Itasca, Ill.).

Paraffm sections of corneal buttons from patients with pseudophakic (PBK) or aphakic (ABK) bullous keratopathy, corneal scar, Fuchs' corneal dystrophy, lattice corneal dystrophy, macular corneal dystrophy, and granular corneal dystrophy are employed as an additional set of controls. The keratoconus, normal human, and diseased specimens, as well as their negative controls, are always stained simultaneously under identical conditions, and comparisons are made on all sections stained at the same time in one experiment. Immunostaining experiments are repeated at least three times to confirm the results. In some experiments, cryostat sections from freshly frozen corneas are used.

Immunohistochemical staining patterns and intensity are analyzed with a Zeiss scanning electron microscope-image processing system (SEM-IPS; Carol zeiss, Thronwood, N.Y.) established and calibrated (21) in Dr. Paul Knepper's laboratory. Quantitative measurements are made as percent of transmission with a planapochromatic 40X oil-immersed objective using a Zeiss scanning microspectrophotometer with the wavelength set at 500±10 nm. For each layer of the corneal specimens, measurements on five cells from different fields are made. These measurements are highly reproducible. The transmission values measured are used to calculate the absorbance values by A=log 1/T, where A is the absorbance and T is the percent transmission value. Data obtained from keratoconus and from the central portion of normal human corneas are calibrated against the nonspecific background values obtained with nonimmune normal serum. Results are analyzed by grouped Student's t-tests.

For correlative Western blot and dot blot analyses, the central region of normal control corneas is obtained using a 7.5-mm trephine. These pieces, as well as keratoconus and other diseased corneas, are separated into stromal and epithelial layers, and each layer is pulverized in liquid nitrogen and homogenized at 4° C. in 150 $\mu$l (for epithelial layer) or 500 $\mu$l (for stroma) of 0.1 M tris buffer, pH 7.2, and 0.154 M NaCl, using a motorized glass homogenizer. Aliquots of the homogenates are taken for measurements of DNA content. (24) In some samples, 0.05% hexadecyltrimethylammonium bromide is added to the homogenates. The homogenates are centrifuged at 4° C. at 27,00 g for 20 minutes. The protein contents in the supernatants are measured by Bradford's protein assay (Bio-Rad, Richmond, Calif.) using bovine serum albumin as a standard. The amount of protein contained in the pellets is determined after solubilization in 0.2 M NaOH and 0.2 M NaOH and 0.2% sodium dodecyl sulfate.

For Western blot analyses, aliquots of the supernatant fractions (10 $\mu$l) and target antigens (e.g., $\alpha$2-M) are electrophoresed on 6% sodium dodecyl sulfate gels under reducing conditions. The proteins are electroblotted overnight onto a nitrocellulose membrane (0.2 $\mu$m; Schleicher & Schuell, Keine, N.H.). After blocking with 5% nonfat dry milk (Carnation, Los Angeles, Calif.), the membrane is allowed to react with either the antibody probe (e.g., rabbit anti-$\alpha$2-macroglobulin—1:10,000; Dako) or IgG (e.g., rabbit IgG—1:10,000; Cappel, Durham, N.C.), followed by incubation with secondary antibody (e.g., goat anti-rabbit IgG conjugated to horseradish peroxidase—1:10,000; Cappel). Immunoreactive bands are visualized using the luminol-based enhanced chemiluminescence (ECL) system (Kirkegaard & Perry Laboratories, Gaithersburg, Md.) and recorded on x-ray film (Konica, Tokyo, Japan). Prestained molecular weight markers (Bio-Rad) were run in parallel.

For quantitative dot blot analyses, aliquots (50 $\mu$l, in serial dilutions) of each corneal sample are loaded onto a nitrocellulose membrane in a 96-well dot blot apparatus (Bio-Rad). Appropriate standards (e.g., $\alpha$2-M; Athens) are selected. Immunodetection is carried out as described above. The labeled spots visualized by ECL are quantified by a microplate reader (Biotek, Burlington, Vt.). Data from triplicate samples are averaged. Non-specific binding is determined on duplicate blots incubated with only normal rabbit IgG and the secondary antibody. These are subtracted from the total binding to determine the specific binding. Resultant values are then compared with the standard curve obtained with known amounts of the inhibitor. The dot blot values are all normalized to the DNA content. Analysis of variance is used to determine the statistical significance of the data.

In conjunction with the foregoing assays, antiproteolytic activity may be closely defined in terms of quantitative differences in morphological and/or ultrastructural features attributable to proteolytic activity between test and control corneal tissues. Exemplary indicia in this context include quantitative changes in the extent of fragmentation of Bowman's layer, fragmentation of the epithelial cell basement membrane, and/or fibrillation of the anterior corneal stroma. These indicia can be readily identified using the immunohistochemical methods set forth above, particularly with the use of additional immunological reagents to detect proteins and glycoproteins specific to individual corneal layers (e.g., Bowman's layer) to specifically demarcate histopathological changes (e.g., sites of fragmentation of stromal or Bowman's layers) within treated and control samples. Particularly useful within this context are a variety of histopathological computer-aided image analysis programs that resolve percentages of optical field areas occupied by immunochemically labeled structures (e.g., proteolytically altered versus normal histological structures).

By applying the foregoing procedures and principles, it will be shown that the antiproteolytic compositions and methods of the invention effectively treat corneal disease in a mammalian patient. In particular, the assays utilized herein enable demonstration that antiproteolytic compositions of the invention provide quantitative inhibition of structural degradative changes in the corneas of patients suffering from keratoconus. Correlative assays set forth above allow further demonstration that these structural inhibitory effects are correlated with substantial reduction of specific proteolytic activity within targeted corneal tissues, which effects are in turn attributable to the activity of exogenous protease inhibitors administered according to the methods of the invention. Within these methods, preferred embodiments involve administration of the inhibitor(s) to a subject during a period of closed eye tear production.

EXAMPLE III

FORMULATIONS FOR TOPICAL OCULAR DELIVERY OF PROTEASE INHIBITORS

A variety of topical antiprotease formulations are useful within the methods of the invention, including solutions, gels, creams, particulate suspensions, and the like. For example, eyedrops comprising an aqueous protease inhibitor solution isotonic with tears are particularly useful for repeated instillation during periods of reflex tear production. However, poor bioavailability of drugs and other therapeutic agents in topical ophthalmic preparations limits therapeutic drug delivery and efficacy from aqueous solutions and other topical formulations. Poor bioavailability is attributable to a variety of factors, including rapid clearance of therapeutic agents by tear flow, neutralization or degradation of therapeutic agents by proteases and other mechanisms, barriers to diffusion and penetration of therapeutic agents across the corneal epithelium to reach the corneal stroma and other intraocular compartments, etc. To overcome these shortcomings, the invention provides novel delivery systems that not only prolong ocular residence time, but also enhance drug transport to intraocular target sites (e.g., corneal epithelia, stroma, Bownan's layer and vitreous humor compartments). In addition, the delivery systems are safe and non-irritating and provide other advantages that promote patient compliance.

i) Mucoadhesive Polvmer Formulations

To address the foregoing delivery issues, the invention provides protease inhibitor compositions wherein the protease inhibitor is dissolved, suspended, or admixed with a delivery vehicle or carrier comprising an opthalmically acceptable, mucoadhesive polymer. Mucoadhesive polymers that adhere to mucinepithelial surfaces have recently gained attention in ocular drug delivery (Hui et al., *Int. J. Pharm.* 26:203–213, 1985; Gurny et al., *J. Contr. Rel.* 6:367–373, 1987; Saettone et al., *Int. J. Pharm.* 51:203–212, 1989; and Davies et al., *Pharm. Res.* 8:1039–1043, 1991, each incorporated herein by reference). As used within the compositions and methods of the invention, mucoadhesive carriers prolong contact between the subject protease inhibitor(s) and the underlying absorptive tissue. At the same time, the mucoadhesive carrier functions integrates with, or replaces, naturally adhering mucin until the latter is replenished, which intensified contact weakens barrier properties of the epithelium and results in facilitated penetration of the protease inhibitor(s). These properties of mucoadhesive polymer delivery systems within the invention can be readily determined and optimized in accordance with the following exemplary protocols. These protocols all specifically demonstrate that mucoadhesive polymers, e.g., polycarbophil (a derivative of polyacrylic acid loosely cross-linked with divinylglycol) improves ocular delivery of protease inhibitors in an accepted model system for corneal delivery using the pigmented rabbit.

Materials

A range of mucoadhesive polymers are available and may be obtained from a variety of commercial sources. For the present example, Polycarbophil (Noveon AA-1) is obtained from BF Goodrich (Cleveland, Ohio). Protease inhibitors are obtained from various sources, as exemplified above. Protease inhibitor levels are measured by any of the foregoing methods or, alternatively by fluorescence polarization immunoassay using a TDx system (Abbott Laboratories, Diagnostic Division, Irving, Tex.).

Preparation of Test Formulations

Multiple test formulations are prepared by mixing a selected protease inhibitor with various vehicles, including (1) a 0.81% (wt/vol) NaCl solution; (2) 0.81% (wt/vol) NaCl and 4.5% (wt/vol) polycarbophil in a polycarbophil (PCP) formulation; and (3) 0.81% (wt/vol) NaCl and 4.5% (wt/vol) polycarbophil adjusted to pH 7.5 with 10 N NaOH in a pH adjusted PCP formulation. Due to the presence of swollen but undissolved polymer, the PCP formulation-at pH 2.5- appears as an opalescent, slightly viscous solution. By contrast, the pH adjusted PCP formulation forms a transparent, highly viscous gel. The buffer capacity of the PCP formulation is calculated to be 0.01, comparable to that of rabbit tears.

Any one or more of the above enumerated protease inhibitors may be included in the mucoadhesive formulation. In the present example, α2-M and alp1 are combined in a series of mucoadhesive formulations, with each inhibitor provided in a range of concentrations therein (e.g., 0.2, 0.5, 1.0, 5.0, 10, and 100 µg/ml).

Release of Protease Inhibitor In Vitro

Fifty-microliter aliquots from each formulation are added to 5 ml of glutathione-bicarbonate Ringer's solution of pH 7.4 in a test tube, vortexed for 30 seconds, and kept in a water bath at 37° C. with occasional shaking. At predetermined intervals, the test tubes are centrifuged at 2,500 g for 2 minutes to sediment the polymer particles. A 50 µl sample is withdrawn from the supernatant and assayed to determine concentrations of protease inhibitor(s) after making a 20-fold dilution with TDx-buffer. The test tube is vortexed again to disperse the polymer, and incubation is continued.

Drug Delivery In Vivo

Dutch-belt pigmented type rabbits, each weighing approximately 2 kg, are used. All experiments involving rabbits conform to the ARBO Resolution of the Use of Animals in Research. No attempt is made to remove the nictitating membrane, because of the possibility that the nature of the surgical procedure might confound the experimental results. Moreover, the nictitating membrane has already been shown not to affect the extent of ocular absorption of topically applied pilocarpine, epinephrine, and chloramphenicol. Even if this were not the case for protease inhibitors, comparative evaluations of different delivery formulations should not affected.

Rabbits are kept upright in minimally restraining cases throughout the experiment. The protease inhibitor formulations (25 µl) are instilled using an Eppendorf pipette (Brinkman Instruments, New York, N.Y.) at the upper lid of each eye, with the exception of the highly viscous, pH adjusted PCP gel. In this instance, the formulation is instilled into the lower cul-de-sac using a multiple dose, positive displacement pipette (Eppendorf Multipette). Unless otherwise indicated, neither topical nor systemic anesthesia is used.

At predetermined times (e.g., 2 hr, 4 hr, 8 hr, 16 hr, and 24 hr), rabbits are killed by injecting an overdose of Na pentobarbital solution into the marginal ear vein. The eyeballs are immediately enucleated. Aqueous and vitreous humor samples are obtained by aspiration with a tuberculin syringe through a hypodermic needle, and corneal tissues are harvested for further study. After carefully rinsing the surface of the tissue samples with a 1.17% KCl solution to remove residual drug-containing vehicle, the samples are gently wiped and weighed. All samples are kept at −70° C. until assay.

To determine the role of the corneal epithelium in corneal penetration of protease inhibitors, the corneal epithelium is removed before administration of the mucoadhesive formulation by carefully scraping with a lancet blade under topical anesthesia elicited by 25 µl of proparacaine (0.025%) and general anesthesia elicited by an intramuscular injection of ketamine (100 mg/kg) and acepromazine (10 mg/kg).

Aqueous humor and vitreous humor samples are assayed directly utilizing appropriate immunological assays, whereas corneal tissues are subjected to initial processing and protease extraction, as described above.

In accordance with the above methods, the invention provides novel delivery systems comprising a protease inhibitor dissolved or suspended in a mucoadhesive polymer. These compositions are readily optimized in terms of consistency and inhibitor concentration so as to maximally prolong ocular residence time and enhance transport of protease inhibitors and coordinately administered agents to intraocular target sites (e.g., corneal epithelia, stroma, Bowman's layer and vitreous humor compartments). In addition, the delivery systems are safe and non-irritating and do not excessively obstruct visibility, thereby promoting patient compliance and efficacy of treatment.

ii) Microparticulate Delivery Formulations

Although mucoadhesive polymer formulations provide useful vehicles for prolonged ocular delivery of protease inhibitors, microparticulate technology is also shown to provide preferred, long-term ophthalmic delivery vehicles for use within the invention. Methods of the invention which utilize microparticulate formulations as delivery vehicles for antiproteases are particularly amenable to use during periods of closed eye tear production (e.g., overnight use), further optimizing these novel methods of the invention.

Microparticulates of the invention are small polymeric particles (erodible, non-erodible or ion exchange resins) suspended in a liquid carrier medium. These particles contain one or more protease inhibitors in an antiproteolytic effective concentration. Upon administration of the microparticulate suspension in the eye, the particles reside at the delivery site (cul-de-sac, sub conjunctiva or vitreous cavity) and the protease inhibitor(s) is released from the particles through diffusion, chemical reaction, polymer degradation, or ion-exchange mechanism.

Several distinct approaches have been used to formulate therapeutic agents in microparticulate dosage form for intraocular and topical application. These include erodible microparticulates, pH responsive microparticulates, nonoparticles/latex systems, ion-exchange resins, etc. Injection of bioerodible microparticulates into the vitreous humor can also be employed for treating corneal disease according to the methods of the invention, whereby release of effective levels of protease inhibitors can be sustained for long-term periods of 2–3 days and up to two weeks or more. Both corneal and non-corneal routes of entry into the eye from topical instillations of microparticulates are possible. Within the invention, this dosage form is particularly well suited to sustained-term delivery (e.g., 4–8 hr, preferably 8–12 hour, more preferably 12–24 hr), and therefore provide optimal delivery during closed eye tear production periods.

Two general microparticulate forms employed for ophthalmic delivery of antiproteases are microcapsules and microspheres. Particles or aqueous droplets of proteases are entrapped inside a polymeric membrane of microcapsules, yielding almost spherical entities on the order of several hundred microns in diameter. Microspheres are polymeric combinations where the protease inhibitor is homogeneously dispersed in the polymer matrix. Nanoparticles possess similar characteristics of microspheres except that their size is approximately three orders of magnitude smaller. Particles ranging from 100 nm to the order of several hundred microns are included in the microparticulate vehicles of the invention.

Liposomes, which are synthetic microscopic sacs of aqueous interior surrounded by phospholipid bilayer membrane, are also useful in this category. Indeed, the use of any non-aqueous lipid miscible carrier, for example, such as prepared with liposomes are particularly advantageous since they provide improved activity at ocular treatment sites.

In recent years, liposomes have been increasingly explored as drug delivery systems. Depending on size, composition and surface characteristics, liposomes interact specifically with biological structures. Liposomal drug products provide a topical activity at the desired locus of action and are found to have excellent tolerability and lack of immunogenicity compared to conventional drug formulations. For ocular use, liposomes also associate closely with lipophilic surfaces in the eye, enhancing retention and delivery. In addition, liposomes provide a moist molecular film for the treatment environment. The multilamellar vesicles of liposomes also act as microreservoirs, hence further prolonging the release of the active ingredient.

Topical delivery or instillation of microparticles is accomplished via conventional commercial eye dropper, an attractive feature for patient acceptability and compliance. For intraocular application, the microparticulate suspension has an advantage of deliverability of antiproteases to the target site through a 27 gauge needle, rather than an involved surgical procedure that is required for device implants.

Time Constant for Chemical Reaction

Release of protease inhibitors through bioerodible polymers is a function of the rate of hydrolysis of the acid or base labile linkages of the polymer and the subsequent release of the protease inhibitor via diffusion through the pores of the matrix created by the polymer hydrolysis. As expected, the time constant for chemical reaction, trxn, is of importance for such systems whose performance rely on polymer hydrolysis. It is defined as the ratio of change in polymer concentration to the average chemical reaction rate during the time over which the concentration change is observed (Joshi et al., *J. Ocular Pharmacol.* 10:29–45, 1994, incorporated herein by reference). For example, if the rate of hydrolysis for the polymer is observed to be first order with the rate constant of 0.05 hjr-1, the time constant for chemical reaction is 20 hours indicating extremely slow polymer degradation rate and prolonged release of the inhibitor. Care should be taken to design bioerodible systems as evaluation of multiple time constants of reaction and diffusion is required to establish their performance (9). The slowest time constant of these two competing rates determines the rate limiting step and the system performance. A useful mathematical parameter to determine the rate limiting step for bioerodible systems is the Thiele modulus, ø:

$$\varphi^2 = \text{time constant for diffusion/time constant for reaction} = t_{dif}/t_{rxn}$$

When the magnitude of the Thiele modulus, ø, is greater than unity, the diffusion process is rate limiting; when ø is less than unity the reaction process is rate limiting.

Microparticulate systems rely on release of protease inhibitors and other therapeutic agents due to diffusion, reaction, physical erosion and ion exchange at the delivery. Each physical or chemical event operates on its own characteristic time scale and the overall process or performance of the delivery system is a result of integration of these events occurring on several time scales. Time constant analysis is a useful tool to sort the time scale hierarchy of mechanism controlling inhibitor release, thereby allowing the designer to focus on those rate limiting parameters that are of interest to achieve prolonged residence and delivery time.

Inhibitor loaded microparticulates suspended in aqueous or non-aqueous medium are preferably instilled topically in the cul-se-sac of the eye by conventional eye dropper. These particles are retained in the cul-de-sac where the inhibitor is slowly released in the lacrimal pool by dissolution and mixing, diffusion or mechanical disintegration/erosion of the polymer matrix. The presence of these particles may stimulate reflex tear rate varying between 3 μl to 400 μl per minute. Blinking of the eyelids facilitates spreading of the protease inhibitor in the lacrimal pool over the cornea.

The movement of upper and lower eyelids during blinking and the force of approximately 0.2 N to 0.8 N that is estimated to open and close the eyelids over the cornea results in an enormous shear rate of about 20,000 sect$^{-1}$. The change in size, shape and partial disintegration of the particles that are exposed to this force and shear rate may alter the in vivo release of the inhibitor that is predicted or extrapolated by in vitro release kinetics experiments. The primary route by which the protease inhibitor reaches the site of action is the cornea (Lee et al., *J. Ocular Pharmacol.* 2:67–108, 1986, incorporated herein by reference). However, the particles may demonstrate a tendency to agglomerate and accumulate in the fornices, or, the released inhibitor from the particulate may be held in proximity to the conjunctive or sclera. In this situation, it is postulated that the inhibitor may enter other compartments of the eye through the scleral route.

The following different approaches can be used to formulate protease inhibitors (and other drugs in combinatorial formulations) in microparticulate dosage form for topical administration.

Polymer-Inhibitor Complex

Polymer-inhibitor complexation involves covalent or chemical linking of the protease inhibitor(s) to the polymer backbone forming a macromolecule pro drug. The covalent bonding can alter solubility of the complex compared to the parent polymer (Heller, *CRC critical Reviews in Therapeutic Drug Carrier Systems*, CRC Press Inc., 1(1):39–90, 1984, incorporated herein by reference). Release of the inhibitor from the complex depends upon the solubility of the polymer, the hydrophobicity of the polymer, the diffusivity of water in the polymer matrix, the hydrolysis rate of the inhibitor-polymer linkage, and the diffusion rate of the inhibitor from the polymer backbone after hydrolysis. The slower of the two processes, i.e., diffusion versus reaction, with a larger time constant determines the rate limiting step for the inhibitor release.

Microspheres of methylprednisolone linked to hyaluronate esters have been studies for topical ophthalmic delivery. Hydrocortisone, hydrocortisone hemisuccinate, benzyl alcohol, mafenide acetate, and sodium fluorescein are model drugs which have been chemically linked to the hyaluronic acid polymer backbone. It is important to choose a polymer backbone which along with its degradants is non toxic and safe for therapeutic application. Hyaluronic acid, being a natural amino-sugar containing mucopolysaccharide and an ubiquitous component of vitreous, aqueous humor and connective tissues, is a relatively conservative and safe choice.

Microspheres

The use of erodible, non-erodible and lipid microspheres for ophthalmic delivery has been described (Lee et al., *J. Ocular Pharmacol.* 6:157–169, 1990, incorporated herein by reference). In the present example, the antiprotease is homogeneously dispersed (monolithic system) in the polymer matrix. As such, the loaded microparticles are then suspended in a liquid carrier medium, which may also include the protease inhibitor.

Ophthalmic bioerodible microspheres ranging from 10 to 200 μm in diameter are disclosed in U.S. Pat. Nos. 4,865,846, and 4,001,388, each incorporated herein by reference. Suitable polymers for use within the microspheres of the invention include poly(esters), poly(orthoesters), poly (peptides), chitosan, poly(lactic) acid, poly(glycolic) acid, copolymers of lactic and glycolic acid, and collagen, among others. These polymers are suitable for release of proteins of different sizes, including full length protease inhibitors and active polypeptide fragments of protease inhibitors.

Different ratios of fatty acid dimer and sebacic acid of varying molecular weights may be copolymerized for microsphere preparation. The in vitro release of protease inhibitors from microspheres depends upon the particle size, cross-linking density and protease inhibitor loading. Within the formulations of the invention, near constant or zero order release rates for one week or more can be obtained using these microspheres.

The pH and osmolarity of the liquid medium in which the microparticles of the invention are suspended should be acceptable to the eye, and the dosage form should be comforting and non-irritating to the user. Also, the polymer and polymer degradants must be non toxic to the eye.

Responsible Multiparticulates

Another preferred ophthalmic microparticle dosage form within the invention are microspheres that undergo significant swelling behavior in response to the changes in pH and temperature of the environment. The particle swelling results in increased viscosity of the formulation in situ, thereby prolonging the dosage form cornea contact time. Inhibitor impregnated ultra fme microspheres of methyl methacrylate and acyclic acid polymer with diameters ranging from 0.2 to 1.0 μm exhibit substantial increased swelling from pH 2.5 to pH 10.0. these microspheres undergo swelling between 13 to 112% with a response time of the order of microseconds, thus making it particularly useful or topical ophthalmic delivery.

Polymeric compositions of poly(lactic) acid (L and D form) and liquid crystalline polymer (polyoxyethyelene glycerol tristearate) in microsphere dosage form may also enhance ocular delivery of protease inhibitors. These compositions have inherent ability to modulate inhibitor delivery/release rates in response to small temperature changes in the environment. Thermoresponsive microspheres provide a pulsatile release in a multistep fashion when the temperature of the environment is fluctuated between 37° C. and 43° C.

In-Situ Gelling Latex Nanoparticles

These systems are comprised of antiprotease impregnated nanoparticles suspended in a carrier medium and ready to be directly administered into the eye. The protease inhibitor can be either chemically bound to the polymer backbone or entrapped in the polymer matrix. The preparation of latex particles of 250 to 300 nm involves emulsification of polymer in organic solvent followed by solvent evaporation, whereafter the inhibitor may be adsorbed onto the particles. Cellulose acetate hydrogen phthalate polymer is an exemplary material for latex particle preparation.

The latex suspension, when instilled into the eye, and upon coming in contact with the lacrimal fluid at pH 7.2 to 7.4 gels in situ and is thus resistant to rapid wash out of the instilled solution from the eye. The gelled polymeric dispersion then slowly releases the bioactive agent. In vivo study of 4% pilocarpine latex preparation resulted in approximately 50% increase in the bioavailability compared to the solution. Since latex preparations consist of up to 30% w/v of the polymer, the topical ocular administration may result in transient vision blurring, caking of the eyelids and forceful closing of the eye due to the viscid nature of the preparation.

Ion-exchange

Long-term delivery rates are difficult to achieve for delivery systems for which diffusion limits the release of the antiprotease. The time constant for diffusion is dictated by diffusional length of the diffusing species, which is small for ophthalmic systems because of the limitation on necessarily small particle size for ocular comfort. The diffusivity of antiproteases in the polymer can be changed, but to have a significant impact on delivery times and rates requires change of diffusivity of several orders of magnitude.

Ion exchange delivery systems provide a suitable alternative to circumvent the limitations of diffusional dependent antiprotease release. The availability of free protease inhibitor for diffusion is limited by the exchange kinetics between the inhibitor and the ion exchange resin and the adsorption isotherm. A modified basic inhibitor is loaded on to the cation exchange resin particles which are of the order of 50 μm. When instilled into the eye, the release of inhibitor which is bound on the cationic resin is accomplished in the eye when the inhibitor, as a free base, is exchanged for monovalent cations such as Na or K present in the tear pool. The net release time of the inhibitor in the eye is controlled by the ion-exchange reversible equilibrium time followed by the diffusional time of the inhibitor through the resin matrix.

Reduction in the diffusivity of the inhibitor once released from the resin surface can be achieved by incorporating the inhibitor loaded resin particles in a viscous medium acceptable to the eye. A successful ocular sustained release system based on ion-exchange principle was recently described in U.S. Pat. No. 4,911,920, incorporated herein by reference. Release of positively charged proteins and peptides from proteinaceous microsphere has also been reported (Kwon et al., *J. Control. Rel.* 22:83–94, 1992, incorporated herein by reference).

Multiparticulate Manufacture and Formulation

Microparticles can be manufactured using several techniques (Wichert et al., *J. Control. Rel.* 14:269–283, 1990; Kitchell et al., *Methods Enzymol.* 112:436–448, 1985; and Schindler et al., *Top. Polym. Sci.* 2:251–281, 1977, each incorporated herein by reference). These include cross linking of the dispersed polymer matrix, solvent evaporation/extraction method, or polymer melt method. For the most commonly used solvent evaporation method, the polymer of interest is dissolved in an organic solvent, suspended in a suitable water or oil medium, and the solvent is extracted from the droplets. The particles obtained after solvent evaporation are recovered by either filtration, centrifugation or lyophilization.

There are several important considerations in the manufacture of microparticles. First, the complete removal of the organic solvent that is used to dissolve the inhibitor in the polymer. Commonly used organic solvents are dichloromethane or methylene dichloride, acetone, acetonitrile and tetrahydrofuran; each of them having a toxic profile and are irritating to the eye. Further production of methylene dichloride has negative environmental ramifications and health hazards. Second, the ability to produce microparticles of uniform size can be a major technical challenge as it requires optimization of several processing parameters such as consistent loading of inhibitor, polymer solvent viscosity, mixing speed, volume of droplet phase, rate of solvent removal, selection of acceptable stabilizer, etc. Hydrolysis of polymer and its control during the manufacturing process may present a difficult and almost unsolvable problem if the chemical degradation kinetics of the polymer are not well understood.

The issue of solvent use is circumvented by fabricating microparticles with molten method technique. However, this technique is plagued by the stability issue relating to both the protease inhibitor and the polymer. The inhibitor is incorporated in the polymer by preparing polymer melt at as high as 180° C. Exposure to high temperatures results in polymer breakdown to smaller units yielding polymer of different average molecular weight than the parent polymer. this leads to the another issue of identifying all the polymeric units after polymer breakdown and evaluation of their toxicological profile, an expensive proposition. Of course, the proper control of temperature and manufacturing parameters are paramount to producing microparticles of uniform size.

For topical delivery, the final formulation must be sterile. The effect of available terminal sterilization methods such as dry heat, autoclaving, radiation, etc. must be carefully studied on the fmal performance of the delivery system. If none of these sterilization techniques are suitable, aseptic manufacturing of microparticles remains an alternative.

By applying the foregoing procedures and principles, it can be readily demonstrated that a macromolecular pro drug delivery system provides for prolonged delivery of protease inhibitors, while achieving lower peak inhibitor concentration and consequently resulting in reduced systemic side effects and higher bioavailability. These delivery systems are useful for sustained ocular delivery of protease inhibitors (e.g., 4–8 hr, preferably 8–12 hour, more preferably 12–24 hr) and are also adaptable for long term delivery (e.g., multiple days and up to one to two weeks). Notably, these delivery vehicles can be readily adapted for optimal delivery of protease inhibitors to the eye to treat corneal disease during periods of closed eye tear production.

EXAMPLE IV

USE OF PRESERVATIVES WITH TOPICAL ANTIPROTEASE FORMULATIONS: PERMEABILITY AND TOXICITY

Deep corneal and intraocular delivery of protease inhibitors is complicated somewhat by the large size of these proteins. Whereas active peptide fragments of protease inhibitors may be efficiently delivered to intraocular compartments, it is more difficult to achieve the same level of penetration with full length antiprotease agents. This problem can be addressed by various modifications of antiproteases, for example by converting the inhibitor to a derivative or salt having higher permeability characteristics, or admixing or conjugating the inhibitor to a permeabilizing carrier, such as a lipid carrier. Alternatively, the topical formulations of the invention can be adapted to include one or more permeabilizing agents.

Various permeabilizing agents are well known and widely used in the art for transdermal delivery systems. These agents, for example, azone or saponin, are generally adaptable for ophthalmic use within the invention, provided that irritation and toxicity levels are determined to be acceptable.

Permeabilizing agents that are found to be particularly useful within the invention include multifunctional permeabilizing agents. As used herein, multifunctional permeabilizing agents enhanced corneal and intraocular delivery of protease inhibitors and also provide a second, preservative or antibacterial function to the antiprotease composition. In this regard, the present example provides methods for selecting preferred, multifunctional permeabilizing agents for use within antiprotease compositions.

In order to evaluate the usefulness of antiprotease formulations containing ophthalmic preservatives, concentrations of the protease inhibitor in tears and corneal tissues are determined for formulations with and without a candidate preservative, before and after instillation of the formulation in albino rabbits, as detailed above. The preservatives used may be any conventional preservative shown to cause acceptable levels of plasma membrane disruption and/or cytotoxicity to eye tissues, for example, benzalkonium chloride, paraben, 2-phenylethanol, benzyl alcohol, sorbic acid, chlorbutanol, disodium edatate, or thimerosal.

Materials

Protease inhibitors, e.g, $\alpha$2-M and alp1, are provided as set forth above. Saponin is obtained from E. Merck (Darmstadt, Germany). Sorbic acid (SA), 2-phenylethanol (PE), methylparaben and propylparaben is obtained from Sigma Chemical Company (St. Louis, U.S.A.). Paraben (PR) is used as a mixture of methylparaben and propylparaben (13:7 w/w). Benzyl alcohol (BA), benzalkonium chloride (BK) and all other chemicals are of reagent grade. Phosphate-buffered saline (pH 7.4) is prepared by mixing an isotonic phosphate buffer with an equal volume of saline.

Animal Subjects

Male Nippon albino rabbits weighing 2.0–3.0 kg are used throughout the study. The animals are maintained as above, but are fasted of solids for 24 h prior to use for the experiments.

In Vivo Instillation Studies

Unanesthetized rabbits are constrained in a prone position, and twenty-five $\mu$l of an antiprotease formulation (ranging in concentration as above) containing preservatives (0.01% BK, 0.04% PR, 0.5% PE, 0.5% BA and 0.25% SA) is carefully applied with a micropipette in the lower conjunctival sac of the subject's eye. Concentrations of protease inhibitors in the tears and corneal tissues is determined by enzyme and/or immunological assays, as above.

Local Toxicity and Irritation

For determining local toxicological effects, rabbit eyes are gently washed 6 h after instillation of the antiprotease formulation. The eyes are subsequently examined and scored according to the scale of Draize et al. (*J. Pharmacol. Exp. Ther.* 82:377, 1994, incorporated herein by reference) 1, 2, 3 and 7 days after the instillation.

Blinking counts are measured as a local irritation index after instillation of the antiprotease formulation containing preservatives (0.01% BK, 0.04% PR, 0.5% PE, 0.5% BA and 0.25% SA). A pH 7.4 buffer is used as a control. 0.1% saponin and 0.1% EDTA are also used as an absorption promoter control. Blinking of the instilled eye, noninstilled eye and both eyes together is counted for 2–5 min.

The foregoing protocols allow demonstration that anti-protease formulations containing ophthalmic preservatives delivered via an ocular route increase the permeability of ocularly administered antiproteases. Thus, these formulations are particularly useful within the invention by their ability to simultaneously stabilize formulations, inhibit microbial infection, and enhance permeability and efficacy of antiproteolytic agents.

The foregoing disclosure sets forth a number of references to patents and other publications which are cited rather than bodily incorporated for economy and ease of understanding of the invention. Each of these publications are incorporated in its entirety within this disclosure for all purposes.

Although the foregoing invention has been described in some detail by way of illustration and example for purposes of clarity of understanding, it will be obvious that certain changes and modifications may be practiced within the scope of the appended claims.

What is claimed is:

1. A method for treating keratoconus in a mammalian subject comprising administering to an ocular surface of the subject a protease inhibitor in an opthalnically acceptable carrier, wherein said protease inhibitor is administered in an antiproteolytic effective amount and duration effective to alleviate a symptom of keratoconus in the subject, wherein said protease inhibitor is selected from the group consiting of $\alpha$2-macroglobulin ($\alpha$2-M) and $\alpha$1-protease inhibitor (alp1).

2. The method of claim 1, wherein the protease inhibitor is $\alpha$2M.

3. The method of claim 1, wherein the protease inhibitor is alp1.

4. The method of claim 1, wherein the protease inhibitor is administered topically.

5. The method of claim 1, wherein the carrier is a microparticulate carrier selected from the group consisting of microcapsules, microspheres, nanoparticles, and liposomes.

6. The method of claim 1, wherein the protease inhibitor is administered during a period of closed eye tear production by the subject.

\* \* \* \* \*